US005496265A

United States Patent [19]
Langley et al.

[11] Patent Number: 5,496,265
[45] Date of Patent: Mar. 5, 1996

[54] BLOOD COMPONENT COLLECTION SYSTEM WITH OPTIMIZER

[75] Inventors: Robert W. Langley, Westminster; John J. Keller; Steven G. Urdahl, both of Golden, all of Colo.

[73] Assignee: Cobe Laboratories, Inc., Arvada, Colo.

[21] Appl. No.: 140,254

[22] Filed: Oct. 21, 1993

Related U.S. Application Data

[63] Continuation-in-part of Ser. No. 912,973, Jul. 10, 1992, abandoned, and a continuation-in-part of Ser. No. 845,677, Mar. 4, 1992, abandoned, and a continuation-in-part of Ser. No. 110,432, Aug. 23, 1993, Pat. No. 5,437,624.

[51] Int. Cl.$^6$ .................................................. A61M 37/00
[52] U.S. Cl. ............................................ 604/5; 604/4
[58] Field of Search ............. 604/4–6, 29; 128/DIG. 13, 128/713; 364/413, 413.07

[56] References Cited

U.S. PATENT DOCUMENTS

| | | | |
|---|---|---|---|
| 4,457,750 | 7/1984 | Hill | 364/413.01 |
| 4,657,529 | 4/1987 | Prince et al. | 604/6 |
| 4,851,126 | 7/1989 | Schoendorfer | 210/651 |
| 4,968,295 | 11/1990 | Neumann | 604/6 |
| 5,024,231 | 6/1991 | Feldschuh et al. | 128/713 |
| 5,178,603 | 1/1993 | Prince | 604/6 |
| 5,324,422 | 6/1994 | Colleran et al. | 604/29 |

FOREIGN PATENT DOCUMENTS

WO84/00112  1/1984  WIPO ............... A61M 1/03

Primary Examiner—Randall L. Green
Assistant Examiner—Rob Clarke
Attorney, Agent, or Firm—Sheridan Ross & McIntosh

[57] ABSTRACT

A blood component collection system with optimization capabilities. In one embodiment, process parameters are derived from an input/configured predetermined blood component yield and which is based upon the maximization of at least one process parameter. Thereafter, the blood component collection procedure is performed with these derived process control parameters. In another embodiment, process parameters are derived from an input total procedure time from a maximized value for at least one of the other process control parameters so as to maximize blood component yield in this fixed time. Thereafter, the blood component collection procedure is performed with these derived parameters.

81 Claims, 9 Drawing Sheets

FIG.6

BLOOD COMPONENT COLLECTION SYSTEM WITH OPTIMIZER

RELATED APPLICATIONS

This application is a continuation-in-part of U.S. patent application Ser. No. 07/912,973, filed Jul. 10, 1992, entitled "METHOD AND APPARATUS FOR PRODUCING BLOOD COMPONENT PRODUCTS," now abandoned, U.S. patent application Ser. No. 07/845,677, filed Mar. 4, 1992, now abandoned, and U.S. patent application Ser. No. 08/110,432, filed Aug. 23, 1993, U.S. Pat. No. 5,437,624, the entire disclosures of which are incorporated by reference herein.

FIELD OF THE INVENTION

The present invention generally relates to the field of blood component collection systems and, more particularly, to providing management capabilities by incorporating optimization principles into such systems.

BACKGROUND OF THE INVENTION

The utilization of blood taken from donors and infused into recipients is well known for purposes of treating medical emergencies and other conditions. More recently, selected blood components have been separated and collected from blood for subsequent infusion into recipients requiring blood component therapy. The primary blood components include platelets, red blood cells, white blood cells, and plasma.

In order to collect blood components, blood is removed from a donor by a needle assembly or other blood access device and is thereafter processed utilizing centrifugation or other appropriate separation techniques to isolate and collect the desired components. This procedure is carried out most effectively in an on-line process wherein blood is removed from a donor, processed through a disposable extracorporeal circuit to obtain the desired components, and thereafter returned to the donor. One blood component collection system which provides for this type of blood component collection procedure is the COBE Spectra™ which is commercially available from the assignee of the present application.

The yield of a particular collection of blood components is an important factor. For instance, presently in the United States a yield must be associated with a collection of blood components in order to be a useful blood component product. COBE Spectra™ presently accommodates for this requirement by processing certain donor biological data such as height, weight, sex, and hematocrit, preconfigured/operator-input data such as the total procedure time, and system-related data such as the type of collection procedure (e.g., single or double needle) and collection efficiency to generate certain process parameters such as the inlet flow to COBE Spectra™ (a combined flow of whole blood from the donor plus typically a flow of anticoagulant) and a predicted blood component yield as well.

An additional consideration presently in the United States relating to blood component yield is that it is determinative of the product classification. With regard to platelets, presently a single platelet product is considered to be a collection of $3 \times 10^{11}$ platelets and a double platelet product is considered to be a collection of $6 \times 10^{11}$ platelets. If the collection is between $3 \times 10^{11}$ and $6 \times 10^{11}$ platelets it is still considered to be a single platelet product. This classification as a single or double platelet product is relevant to blood component collection facilities (e.g., blood banks/centers) since a double platelet product has a higher selling price associated therewith than a single platelet product and also typically benefits more patients. The yield of a particular collection of blood components may also be a relevant consideration for certain therapeutic treatments.

Other important considerations relating to blood component collection systems relate to the donor. For instance, blood component collection facilities are not only experiencing an increase in the overall demand for blood components, but the demand now typically varies between the blood component types as well. Moreover, not only is the supply of donors unfortunately in many cases inadequate, but donor time constraints are becoming more prevalent. Furthermore, obtainable yields from a given donor may vary from one blood component to another (i.e., one donor may be a better platelet source than a red blood cell source).

Based upon the foregoing, the management of the various aspects of blood component collection systems is becoming increasingly important.

SUMMARY OF THE INVENTION

The present invention relates in one application to a blood component collection system which provides management capabilities by incorporating optimization principles. Generally and in this case, the present invention utilizes principles of optimization in terms of the donor, blood component collection system, and/or desired blood component product. For instance, the present invention may be adapted to provide for the collection of a predetermined quantity of at least one predetermined blood component (or more typically the collection of such blood components within a particular range) in a "minimum" amount of time and/or for the collection of a "maximum" quantity of at least one predetermined blood component in a fixed amount of time, all based upon certain process conditions. Moreover, the present invention may be adapted to provide for blood component inventory control by basing donor selection and/or collection procedure selection in terms of the type of blood component to be collected on blood component demand and/or existing inventory. In addition, the present invention may be adapted to provide for further donor management by collecting that blood component type(s) from the donor which provides a maximum yield.

In one aspect, the present invention may be characterized as a blood component collection system having blood component product-based optimization-like capabilities. One embodiment comprises a method for collecting at least one predetermined blood component (e.g., a collection of platelets, red blood cells) from a source of whole blood using a blood component collection system which includes a blood component collection device and which utilizes a collection procedure. More particularly, a desired yield of the predetermined blood component(s) is identified (such yield including a single yield or range of yields) and biological data relating to the source is provided to the blood component collection system. Moreover, a value or magnitude is associated with each of the various process parameters used in the collection procedure. A magnitude of at least one of these process parameters is derived from the biological data and the desired yield. These magnitudes, including all magnitudes of process parameters derived from the desired yield, are input to the blood component collection system. Thereafter, the collection procedure is performed with the blood component collection device and with the input process parameters to collect the desired yield of at least one predetermined blood component(s) from the whole blood source.

In another aspect, the present invention may be characterized as a blood component collection system having time-based optimization-like capabilities. One embodiment of such is a method for collecting at least one predetermined blood component from a source of whole blood using a blood component collection system which includes a blood component collection device and which utilizes a collection procedure. A flow of the whole blood from the source, as well as a flow of anticoagulant, is provided to the blood component collection system and collectively constitutes an inlet flow. In the method, a total procedure time for the collection procedure is identified (e.g., based upon donor time availability). One potential inlet flow to the system is derived from at least this identified total procedure time. Another potential inlet flow to the system is derived which provides an "optimum" collection efficiency and is effectively the apex of a bell-shaped yield/inlet flow curve (i.e., the inlet flow which provides the maximum blood component yield). Consequently, if the total procedure time-based inlet flow is greater than the maximum yield-based inlet flow, and thus is an inlet flow on the decreasing slope portion of the yield/inlet flow curve, the maximum yield-based inlet flow magnitude is used in the performance of the collection procedure. However, if the total procedure time-based inlet flow is less than the maximum yield-based inlet flow, and thus is an inlet flow on the increasing slope portion of the yield/inlet flow curve, the total procedure time-based inlet flow magnitude is used in the performance of the collection procedure.

The subject invention provides greater efficiency in blood component collection and management. For example, the present invention can be used to compare blood bank/center component inventories with projected needs, and adjust collection procedures to meet these needs. Further, the present invention provides benefits to donors. In particular, certain information relating to the donor's physical and medical characteristics may be stored in the system and utilized during subsequent visits by the donor to derive magnitudes for the various process control parameters. For example, for a donor with an anticoagulant intolerance, the magnitude of the anticoagulant infusion rate may be set so as to not exceed the donor's tolerance.

BRIEF DESCRIPTION OF THE DRAWINGS

FIG. 6 is a flow chart of one optimization model for deriving at least one optimal process parameter from a desired blood component yield or from a total procedure time in accordance with principles of the present invention;

DETAILED DESCRIPTION

The present invention will be described with reference to the accompanying drawings which assist in illustrating the pertinent features thereof. One application of the present invention is embodied within a blood component collection system which separates, removes, and collects at least one type of blood component (e.g., platelets, red blood cells, white blood cells, plasma) from a source of whole blood (e.g., a donor) through utilization of a collection procedure derived from a typically site-configured/operator-input goal(s) and the "maximization" of at least one process control parameter. This type of derivation is referred to herein as an "optimization process" and the derived process control parameters are referred to herein as "optimal values."

Figure 1:
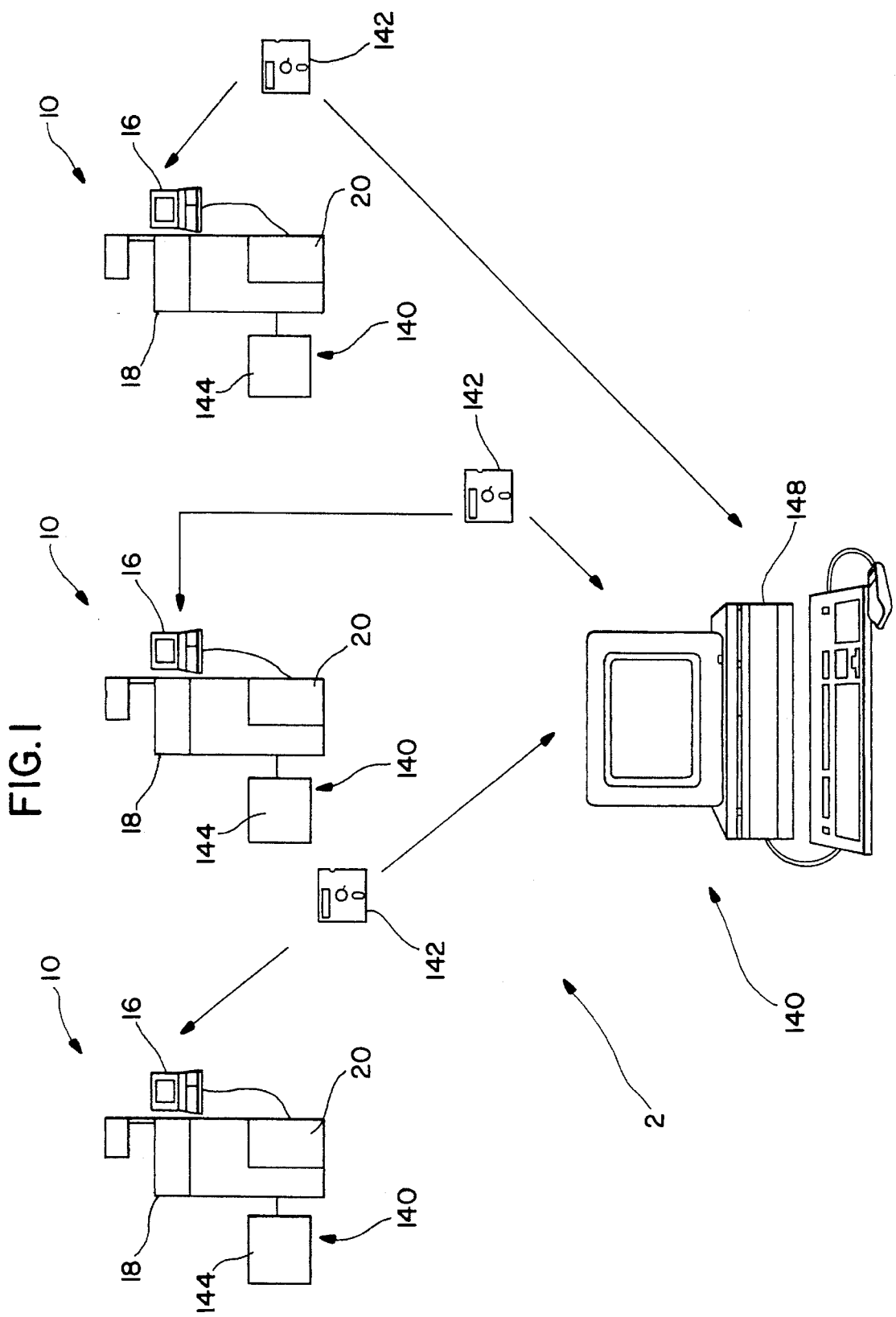
FIG. 1 is a schematic representation of a blood component collection system in accordance with principles of the present invention.

Referring to FIG. 1, the present invention is embodied within the blood component collection system 2 which would typically be implemented at a blood bank/center (not shown). The system 2 includes an optimization assembly 140 (e.g., appropriate microprocessor(s) such as an IBM compatible PC and software) and at least one blood component collection assembly 10 (three shown) which each includes a blood component collection device 18 as an integral part thereof. As will be discussed below, the optimization assembly 140 (or at least a portion thereof) and associated blood component collection assemblies 10 are preferably appropriately interfaced but may be completely separate as well. That is, optimization procedures in accordance with principles of the present invention are not limited to being performed at any particular location.

Generally, the optimization assembly 140 includes a central input station 148 (e.g., an appropriate microprocessor such as an IBM compatible PC and attendant software) for inputting and maintaining donor-related data, and also typically for preparing an initial procedure order (the process control parameters derived from the donor-related data and other considerations) for a given donor. These procedures may also be performed at the appropriate operator interface module 16 as well such that a central input station 148 is not required. However, where a central input station 148 is used, this donor-related data and/or initial procedure order is transferred to one of the operator interface modules 16 (e.g., an appropriate microprocessor such as an IBM compatible microprocessor and interfaced with the device 18 via an RS232 or other lab specific interface, including the Digital Equipment Corp. PCP 30, which is also known as the DEC pc 325SL and which utilizes a 386 processor) which are located at each blood component collection device 18 and which as noted preferably interfaces with an optimizer module 144 (part of the optimizing assembly 140) for providing the operator with one or more optimization options. These optimization options provide a different set of process control parameters than the initial procedure order based upon one or more specified conditions/goals (e.g., input blood component yield, input procedure time) and a particular derivation for the process control parameters. If an optimization option is selected the procedure order is modified to reflect the results of the optimization, the collection procedure is initialized/reinitialized (i.e., the collection procedure would be reinitialized in the case of an optimization which is performed after the collection procedure has been initiated and such is referenced to as a downstream optimization) with the results of the optimization, and the collection procedure is thereafter performed with the blood component collection device 18.

Figure 2:
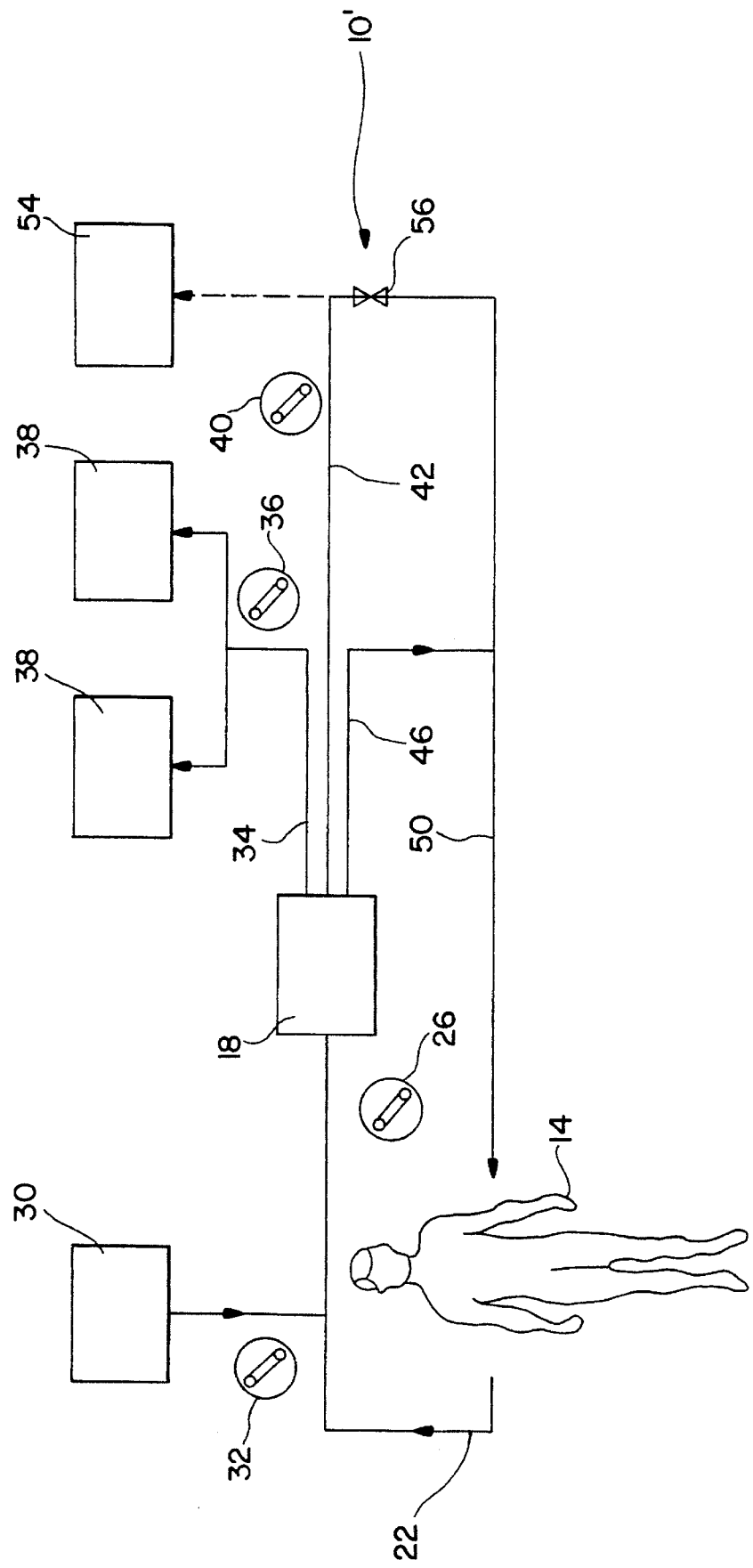
FIG. 2 is a schematic representation of one embodiment of a blood component separation assembly which utilizes a dual needle configuration and which may be incorporated into the blood component collection system of FIG. 1.

Various embodiments of blood component collection assemblies may incorporate principles of the present invention. However, as noted above on-line techniques have been determined to be quite effective and thus the present invention is being described with reference to such techniques. One embodiment of an on-line technique and attendant apparatus which may be incorporated into the blood component collection system 2 of FIG. 1 is illustrated in FIG. 2. The blood component collection assembly 10' utilizes an on-line technique in that a donor 14 (e.g., the whole blood source) is directly integrated with the system 10' by fluid interconnection with the blood component collection device 18. This particular on-line technique is more particularly referred to as a dual needle configuration since there are two fluid interconnections between the donor 14 and the blood component collection device 18.

The donor 14 is fluidly connected to the blood component collection device 18 by an inlet line 22 and appropriate needle assembly (not shown). Whole blood from the donor 14 is thus continuously provided to the blood component collection device 18 through the inlet line 22 for separation of the desired blood component(s) therefrom, utilizing an inlet pump 26 (e.g., a peristaltic pump) to maintain this flow if desired/required. Prior to the blood of the donor 14 entering the blood component collection device 18, anticoagulant from an anticoagulant ("AC") container 30 may be provided to the whole blood, utilizing an AC pump 32 (e.g., a peristaltic pump) to maintain this particular flow if desired/required. Consequently, the inlet flow to the blood component collection device 18 typically includes both a flow of whole blood from the donor 14 and a flow of anticoagulant from the AC container 30.

The blood component collection device 18 separates the whole blood provided on line by the donor 14 into three primary constituents, namely platelets, a combination of red and white blood cells ("RBC/WBC"), and plasma. The platelets collected from the blood component device 18 are directed through a platelet collect line(s) 34 to one or more platelet collect bags 38 via a collect pump 36. The plasma and RBC/WBC are provided back to the donor 14 through a plasma line 42 and RBC/WBC line 46, respectively, both of which are interconnected with a second needle assembly (not shown) on the donor 14 via a donor return line 50. The plasma line 42 includes a plasma pump 40 (e.g., a peristaltic pump) to maintain the flow of plasma if desired/required. Although plasma may be provided back to the donor 14 in the above manner, it may be desirable to collect the separated plasma in some cases. In this regard, a plasma collect bag 54 may be provided and interconnected with the plasma line 42 (interconnection shown in phantom). In this case, appropriate valving 56 may be incorporated in the plasma line 42.

Figure 3:
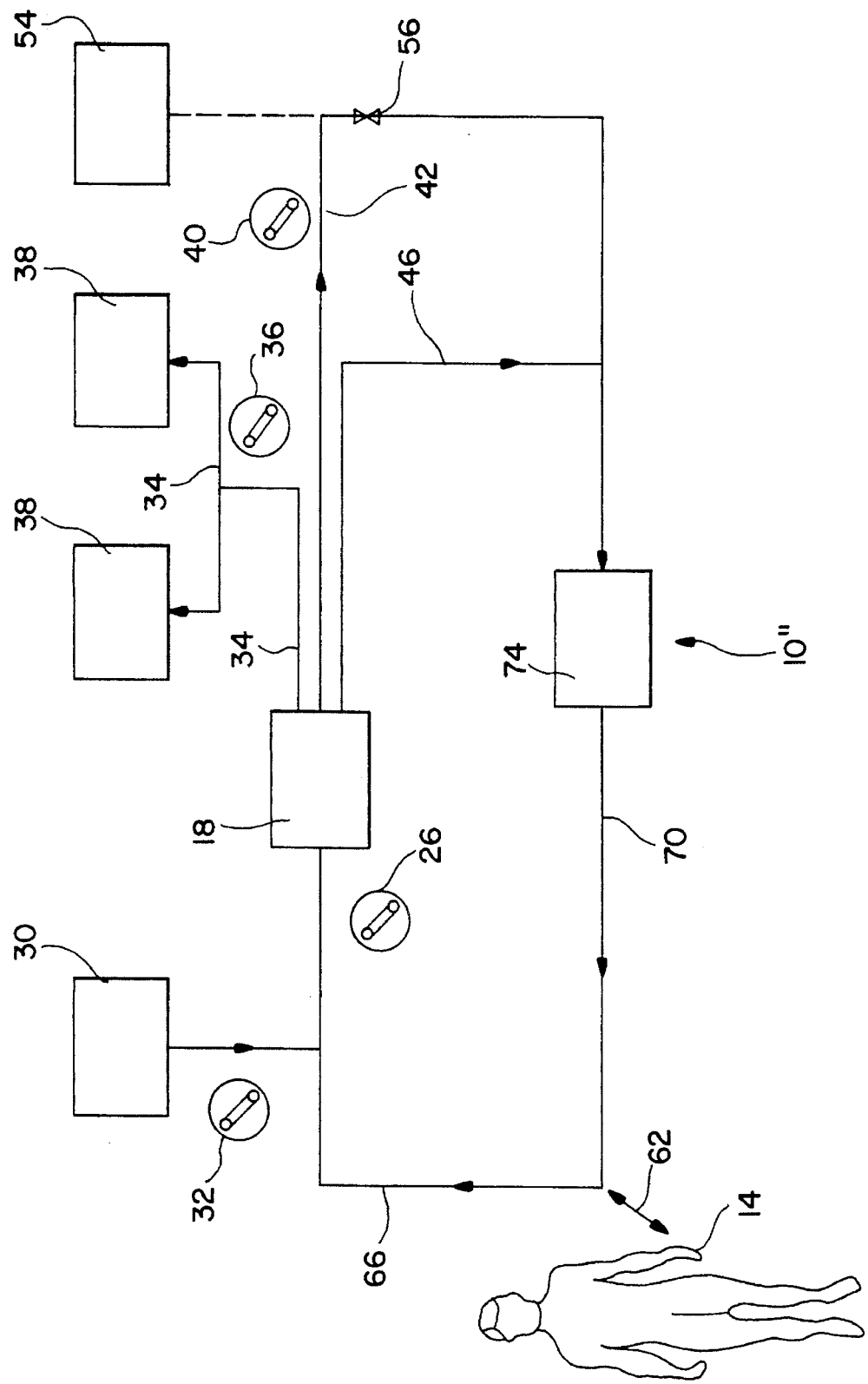
FIG. 3 is a schematic representation of one embodiment of a blood component separation assembly which utilizes a single needle configuration and which may be incorporated into the blood component collection system of FIG. 1.

The blood component separation assembly 10" of FIG. 3 is similar to that of the dual needle configuration of FIG. 2 except that a single needle assembly (not shown) integrates the donor 14 within the blood component collection assembly 10". Consequently, similar components are similarly identified where appropriate. With regard to the single needle configuration of FIG. 3, whole blood of the donor 14 initially flows through a donor access line 62 and into an inlet line 66 which is fluidly connected with the blood component collection device 18 such that the platelets are separated and collected in the above-described manner. The plasma and RBC from the blood component collection device 18 flow through the plasma and RBC/WBC lines 42, 46, respectively, both of which are fluidly interconnected with a return flow controller 74. As above, however, the plasma may alternatively be directed to a plasma collect bag 54. In the event that plasma is not collected, the RBC/WBC and plasma are provided back to the donor 14 through the return flow controller 74 via a donor return line 70 which is interconnected with the donor access line 62. As can be appreciated, since only a single line is directly connected to the donor 14, namely the donor access line 62, blood is either being removed from or provided back to the donor 14 such that the procedure is effectively two-step versus continuous in relation to the donor 14.

Figure 4A:
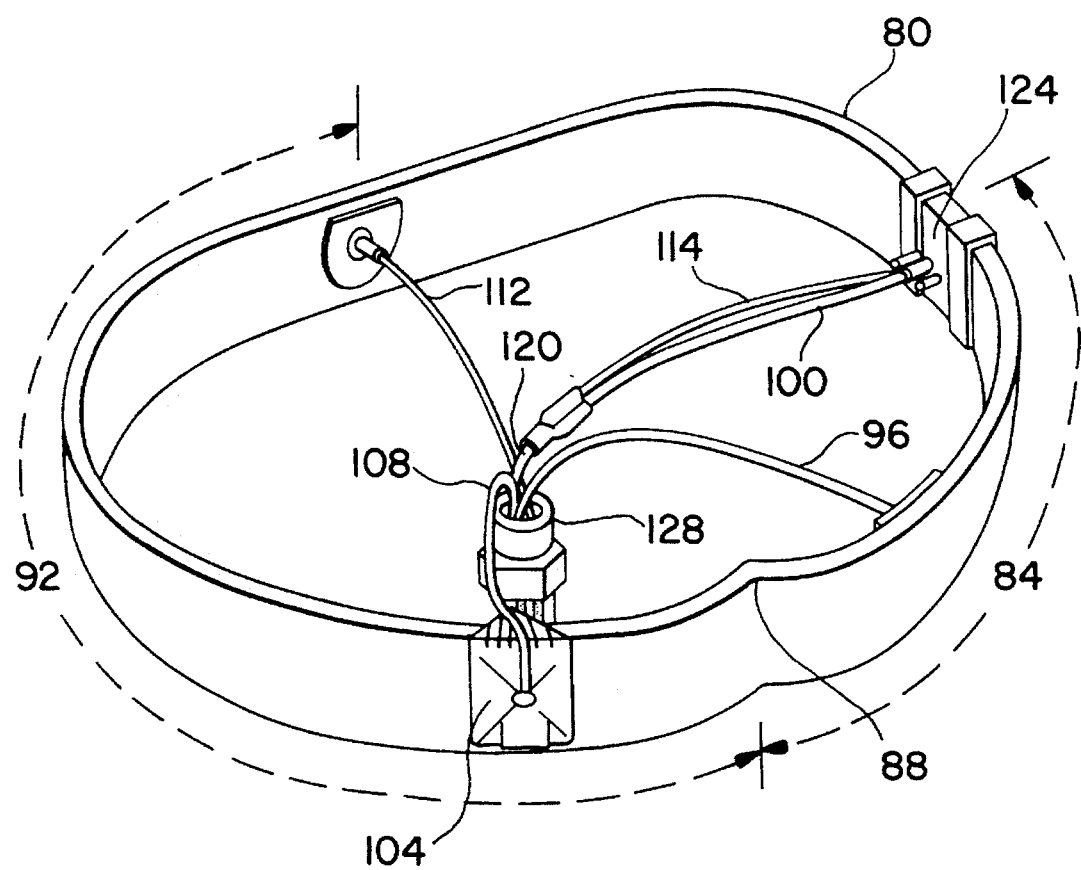
FIG. 4a is a perspective view of one type of a disposable processing channel used in the blood component collection device of FIGS. 2 and 3.
Figure 4B:
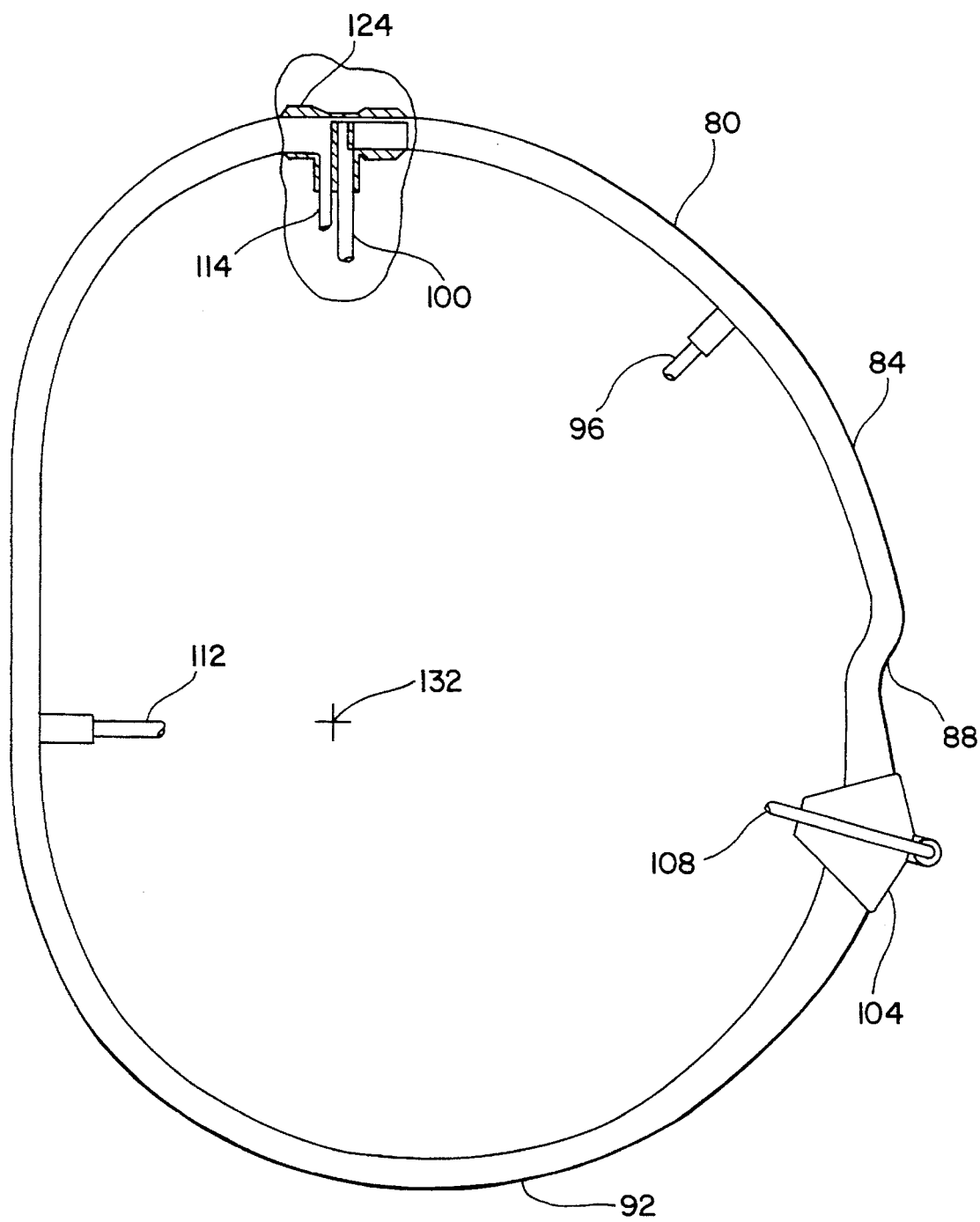
FIG. 4b is a top view of the channel of FIG. 4a; in place thereof.

The blood component collection device 18 used in the blood component collection assembly 10 is more particularly illustrated in FIGS. 4A–B. This device 18 is the subject of U.S. Pat. No. 4,387,848 to Kellog et al., entitled "CENTRIFUGE ASSEMBLY", issued Jun. 14, 1983 and the disclosure of which is incorporated by reference in its entirety herein. This device 18 is also commercially available from the assignee of the present application as such is incorporated in COBE Spectra™.

Referring to FIGS. 4A–B, the blood component collection device 18 utilizes a processing channel 80 to provide the desired disposable extracorporeal circuit. The channel 80 is positioned within a groove formed directly or indirectly in a centrifuge rotor (not shown) (e.g., a separate filler may receive the channel 80 and be attached to the centrifuge rotor), and is illustrated in the shape which it assumes during processing (i.e., during flow of blood therethrough). All subsequent references herein to the structural and operational characteristics of the blood component collection device 18 will be to the processing channel 80 in the illustrated condition.

The processing channel 80 generally includes a first stage 84 for collectively separating red blood cells ("RBC") and white blood cells ("WBC") from platelet-rich plasma, a second stage 92 for thereafter separating platelets from the platelet-rich plasma, a transition portion 88 defining a separation between the first stage 84 and second stage 92, and a control chamber 124 for maintaining a proper interface between the first stage 84 and second stage 92, namely the position of the interface between the RBC/WBC and platelet-rich plasma within the transition portion 88.

The first stage 84 extends from one end of the control chamber 124 along an arcuate path generally inwardly, toward the axis 132 about which the processing channel 80 rotates via the centrifuge rotor, until terminating at the transition portion 88. Specifically, the end of the first stage 84 adjacent the control chamber 124 is positioned at a greater radial distance from the axis 132 than the end of the first stage 84 adjacent the transition portion 88. An inlet tube 96 is fluidly connected with the first stage 84 between its two ends to introduce whole blood into the processing channel 80 and a RBC/WBC tube 100 is provided in the control chamber 124 for removing the separated RBC/WBC from the channel 80. Both the inlet tube 96 and RBC/WBC tube 100 extend externally of the rotatable device 18 for interconnection with the donor 14 and/or collection bags 38, 54.

As RBC/WBC sediment against the outer wall in the first stage 84 during rotation of the centrifuge rotor they are directed and counterflow toward the RBC/WBC tube 100 for removal from the channel 80 due to the increased centrifugal forces at the RBC/WBC tube 100 in comparison with the transition portion 88. That is, since the first stage 84 extends along an arcuate path generally outwardly away from the axis 132 proceeding from the transition portion 88 to the control chamber 124, the centrifugal force differential along the first stage 84 establishes the described counterflow of the separated RBC/WBC. Moreover, the transition portion 88 also assists in providing for this counterflow since it extends along an arcuate path generally inwardly toward the axis 132 proceeding from the first stage 84 to the second stage 92.

The platelet-rich plasma, which has a lower density than the RBC and WBC, flows beyond the transition portion 88 from the first stage 84 into the second stage 92 for further processing, while the RBC/WBC are directed back toward the RBC/WBC tube 100 in the above-described manner. The second stage 92 initiates at the radially inwardmost part of the transition portion 88 and extends along an arcuate path generally outwardly away from the axis 132 to a platelet collection chamber 104. Platelets are removed from the processing channel 80 at the platelet collection chamber 104 by a platelet tube 108 which interfaces with the outer wall of the processing channel 80 at the platelet collection chamber 104. Thereafter, the second stage 92 extends along an arcuate path generally inwardly toward the axis 132 until terminating at the plasma tube 112. Both the platelet tube 108 and plasma tube 112 extend externally of the rotatable device 18 for interconnection with the platelet collect bag(s) 38 and donor 14/plasma collect bag(s) 54, respectively.

Platelets which do not separate from the plasma in the initial portion of the second stage 92 between the transition portion 88 and platelet collection chamber 104 are separated in the portion of the second stage 92 between the platelet collection chamber 104 and the plasma tube 112. These platelets will flow back towards the platelet collection chamber 104 in the opposite direction of the flow of platelet-rich plasma/platelet-poor plasma through the second stage 92 due to the configuration of this portion of the second stage 92. That is, the platelet collection chamber 104 assumes the radially outwardmost position in the second stage 92 such that all platelets, regardless of where separation occurs in the second stage 92, flow towards the platelet collection chamber 104 for removal from the channel 80.

Platelet-poor plasma exits the second stage 92 and flows out through the plasma tube 112 which interfaces with the inner wall of the processing channel 80 and/or continues to flow through the remaining portion of the processing channel 80 to the control chamber 124. Plasma which flows to the control chamber 124 exits the channel through the control tube 114 which joins with the RBC/WBC tube 100 into a single outlet tube 120. The positionings and diameters of the RBC/WBC tube 100 and control tube 114 and the joinder of such into the common outlet tube 120 regulate the position of the RBC/WBC-platelet-rich plasma interface within the transition portion 88 using conservation of mass principles.

The blood component collection device 18 includes a prediction model 20 (appropriately interfaced with the operator input module 16 as shown in FIG. 1 as noted above and which may be used to configure the prediction model 20 and/or to allow operator input of various parameters to be used by the prediction model 20) for predicting a platelet yield before a collection procedure is initiated using a compilation of algorithms. The prediction model 20 may be used by the optimizer assembly 140 which is associated with principles of the present invention and thus will be briefly described herein. Notwithstanding the following discussion of the specifics of the prediction model 20, those skilled in the art will appreciate that the prediction model 20 is associated with the functional and operational characteristics of the blood component device 18 described herein. Therefore, the algorithms used in the prediction model 20 could and likely would vary in the case of other blood component collection devices which may be used by the present invention. Moreover, different algorithms could of course be used even for the prediction model 20. Furthermore, the algorithms are specific to platelet collection and therefore may and likely would change if used in relation to other blood component types such as red blood cells.

The prediction model 20 is typically configured by the site (e.g., the blood bank/center) for a particular blood component collection procedure (e.g., single or dual needle) used by the site and will be presented with regard to the dual needle procedure of FIG. 2 and in relation to a platelet-collecting procedure. In this regard, an AC infusion rate (i.e., the rate at which anticoagulant is provided to the donor 14 per the blood volume of the donor 14) and the AC ratio (i.e., the collective flow of AC and blood through the inlet line 22 in relation to the flow of AC through the line 22) must be specified (through configuration or modified input as will be discussed below). Moreover, in the event that plasma is to be collected into the plasma collect bag 54 in the collection procedure, the maximum amount of plasma which should be collected considering the medical and physical characteristics of the donor 14 must also be provided.

There are two alternatives for establishing the plasma volume limit. The first alternative relating to the plasma volume limit is to provide a weight cutoff (e.g., 0–500 pounds), associated with the weight of the donor 14 which is input as will be discussed below. In this regard, a plasma volume upper limit (e.g., 10–1500 ml.) may be established for a weight of a donor 14 in excess of this cutoff, and a plasma volume lower limit (e.g., 10–1500 ml.) may be established for a weight of such donor 14 which is less than this cutoff. For instance, if the weight cutoff is 175 pounds, the plasma volume upper limit can be 600 ml. for a donor 14 weight greater than or equal to 175 pounds, and the plasma volume lower limit can be 500 ml. for a donor 14 weight less than 175 pounds.

The second alternative for a plasma volume limit is to configure the prediction model 20 such that the plasma volume limit is expressed as a percentage of the total blood volume of the donor 14 which is calculated pursuant to Eq. 10 below. For instance, the plasma volume limit may be established as 1–15% of the total blood volume of the donor 14, and is preferably established as about 12% of such volume.

Further information is required by the prediction model 20 prior to performing its yield prediction function. For instance, the total procedure time is typically input by the operator or preconfigured by the user (e.g., the blood bank/center). When configured the procedure time is typically 100 minutes. Moreover, the total procedure time is affected by whether a stepdown option is utilized for the blood component collection device 18 so as to enhance separation of the various blood components. When this stepdown option is selected, the angular velocity of the blood component collection device 18 is incrementally reduced during the platelet-collection procedure. For instance, the stepdown option could provide for angular velocities for the device 18 of 2400, 2200, and 2000 RPM, each of which would be for a specified duration.

Based upon the foregoing, the configuration of the prediction model 20 in relation to the blood component separation assembly 10' and associated protocol in effect standardizes site protocol for purposes of "normal" operations. However, for a particular donor 14 it may be desirable to alter the "configuration" for one processing run. Consequently, the prediction model 20 utilizes a procedure in which certain parameters utilized in the following equations may be adjusted on a one-at-a-time basis. Such is referred to as modified input data and the associated parameters are procedure time (e.g., 10–999 minutes), inlet flow rate to the device 18 (e.g., 0–150 ml/min. for the FIG. 2 assembly and 0–50 ml/min. for the FIG. 2 assembly), AC ratio option as discussed above (3–50), the desired platelet collect volume (e.g., 10–9999 ml.), the desired platelet collect concentration (e.g., 100–8000×10$^6$/mi.), and the desired source plasma volume to be collected (e.g., 0–9999 ml.). Moreover, other parameters such as AC infusion rate (0.8–1.1), stepdown option (yes or no), needle option (single or double), and high flow option (yes or no) may also be entered as modified input data by an operator.

Having configured the prediction model 20 in the above-described manner, the following additional information is provided and is utilized in the various calculations of Equations 1–22 presented below: (1) needle option, namely whether the procedure is dual needle (FIG. 2) or single needle (FIG. 3); (2) run identification number for purposes of associating the data/output generated by the various equations with a particular donor 14 and processing run; (3) the sex of the donor 14; (4) the height of the donor 14; (5) the weight of the donor 14; (6) the total blood volume as calculated in Eq. 10 below; (7) the hematocrit of the donor 14, either based upon an initial estimation and thereafter updated based upon analysis of the donor's 14 blood sample (e.g., by a cell counter) or input directly from such an analysis; (8) the platelet precount, either based upon an initial estimation and thereafter updated based upon analysis of the donor's 14 blood sample (e.g., cell counter) or input directly from such an analysis; and (9) whether plasma collection is desired in conjunction with the platelet collection.

Based upon the above initial configuration and subsequent data input (except when entered as modified input data), the following output is generated by the prediction model 20: (1) platelet yield; (2) inlet flow rate; (3) AC ratio; (4) procedure time; (5) platelet collect volume; (6) platelet collect concentration; (7) source plasma volume; (8) AC in the platelet and plasma collect bags 38, 54; (9) platelet postcount; (10) AC infusion rate; and (11) output approval. This information is utilized at least in part in the following equations to generate, inter alia, the predicted platelet yield value of the collected platelets for the case of the dual needle procedure of FIG. 2 and also for the case of the single needle procedure of FIG. 3. The differences between those procedures with regard to the prediction model 20 are identified herein. As will be appreciated, some of the equations are utilized in the calculation of the predicted platelet yield, whereas other equations are used to generate additional information for output and informational purposes. The variables or parameters and the units associated therewith of the equations are presented after the equations in the Variables Index.

Platelet Yield:

$$Y = 1 \times 10^6 \, C_{PR} \, V_B \, F_Y \, [1 - exp[\,-E_C \, (f_{BP} - 0.12)]] \tag{Eq. 1}$$

where:

$$f_{BP} = (Q_{IN} \, t_E + 50)(1 - 1/R)/V_B \tag{Eq. 2}$$

and where:

$$Q_{IN} = RQ_{AC} = 0.001 \, I \, V_B \, PR \leq 150 \tag{Eq. 3}$$

Alternatively, the platelet yield may be expressed as:

$$Y = 1 \times 10^6 \, C_{PR} \, V_B F_Y [1 - exp \, [-E_C \, (0.001 \, I \, (R-1) \, Pt_E + 50 \, (1 - 1/R)/V_B - 0.12]] \geq 0 \tag{Eq. 4}$$

Platelet Collection Efficiency:

$$E_C = C_1 - C_2 \, exp \, [9.91 \, (1 - 1/R)H] Q_{INA} \leq 0 \tag{Eq. 5}$$

where the constant $C_1$ is defined as follows:
 $C_1 = 0.803$—dual needle, without stepdown
 $C_1 = 0.840$—dual needle, with stepdown
where the constant $C_2$ is defined as follows:

$C_2 = 4.08 \times 10^{-5}$ — dual needle, without stepdown
 — dual needle, with stepdown and where:

$$Q_{INA} = Q_{IN} \, (t_E/t_P) \tag{Eq. 6}$$

In Eq. 6, $t_P$ may be provided as configuration data or modified data as provided above, or alternatively may be derived from the solution of Eq. 4 for $t_E$.

Effective Procedure Time:

$$\begin{aligned} t_E &= t_P, \, Q_{IN} \leq 45 \\ &= t_P - 500(1/45 - 1/Q_{IN}), \, Q_{IN} > 45 \end{aligned} \tag{Eq. 7}$$

Only high-flow protocol is used for $Q_{IN} > 45$.

AC Infusion Rate Constant:

$$I = 1000 \, Q_{IN}/(PRV_B) \tag{Eq. 8}$$

Alternatively to the use of Eq. 8 for the derivation of the AC infusion rate constant I, such may be provided as configuration or modified input data pursuant to the above.

AC Ratio:

Initially, the AC ratio may be provided as configuration or modified input data pursuant to the above. In configuration, it is defined as follows:

$$\begin{aligned} R &= 1 + 2.51/H & \text{low} \\ &= 1.33(1 + 2.51/H) & \text{medium} \\ &= 1.67(1 + 2.51/H) & \text{high} \end{aligned} \tag{Eq. 9}$$

Total Blood Volume:

$$\begin{aligned} V_B &= 604 + 0.006012 \, L^3 + 14.6 \, W \, \text{ml} & \text{(male)} \\ &= 183 + 0.005835 \, L^3 + 15.0 \, W \, \text{ml} & \text{(female)} \end{aligned} \tag{Eq. 10}$$

Plasma Collect Factor:

AC infusion rate control maintains the AC flow to the donor as:

$$Q_{ACD} = 0.001 \, I \, V_B \quad \text{(Eq. 11)}$$

where the inlet flow associated with this is:

$$Q_{INO} = R Q_{ACD} = 0.001 \, IRV_B \quad \text{(Eq. 12)}$$

$Q_{IN}$ is proportional to the total AC flow, as given by Eq. 3, which includes the AC that flows to the platelet collect bag 38 and the plasma collect bag 54. P (Eq. 13) is the factor by which $Q_{IN}$ is increased by collecting AC, relative to not collecting AC. That is, $$P = Q_{IN}/Q_{INO} = (\text{average } Q_{AC})/Q_{ACD} \quad \text{(Eq. 13)}$$

where:

$$P = 1 + (f_{ACP}/Q_{ACD})\,[V_C/(t_P - 150/Q_{IN}) + V_{SP}/(t_P - 500/Q_{IN})] \quad \text{(Eq. 14)}$$

and where:

$$f_{ACP} = [(R-1)(1-H)]^{-1} \quad \text{(Eq. 15)}$$

Platelet Collect Volume:

$$V_C = 1 \times 10^{-6} \, Y/[C_B(1 + f_{ACP})] \quad \text{(Eq. 16)}$$

Source Plasma Volume:

The four choices provided are as follows:

$$\left. \begin{array}{rcl} V_{SP} &=& 0 \\ &=& V_{CON} - V_C \\ &=& f_{SP} V_B - V_C \\ &=& \text{specified as modified input} \end{array} \right\} \geq 0 \quad \text{(Eq. 17)}$$

where:

$$\begin{array}{rcl} V_{CON} &=& V_{CONL}, \; W < W_C \\ &=& V_{CONH}, \; W \geq W_C \end{array} \quad \text{(Eq. 18)}$$

and where:

$$0.01 \leq f_{SP} \leq 0.15 \quad \text{(Eq. 19)}$$

Donor Postcount:

$$C_{PO} = C_{PR} \exp[-E_C (0.001 \, I \, (R-1) \, Pt_E + 50 \, (1 - 1/R)/V_B - 0.12)] \leq C_{PR} \quad \text{(Eq. 20)}$$

A warning is given if $C_{PO} < 100$.

Collect Volumes:

$$V_{CB} = V_C (1 + f_{ACP}) \quad \text{(Eq. 21)}$$

$$V_{SPB} = V_{SP} (1 + f_{ACP}) \quad \text{(Eq. 22)}$$

The primary equation to be solved for purposes of the yield prediction by the prediction model 20 is Eq. 4. Consequently, Eqs. 1–3 and 5–22 are ancillary to Eq. 4 although they may be used to calculate other output data and/or information required by Eq. 4. With regard to the manner in which Eqs. 1–22 are solved, all the iteration loops are based on the technique of successive approximation, in which each iteration is a repeat of the previous one, but using updated parameter values calculated in the previous iteration. This process continues until all the convergence criteria are met.

The convergence criteria are that, on successive iterations, the variable difference is $\leq 1$ for $V_C$, $\leq 0.2$ for $t_E$, and $\leq 10$ for $C_B$.

As noted above, the foregoing was based upon a dual needle configuration as illustrated in FIG. 2. In the event that a single needle configuration such as that illustrated in FIG. 3 is utilized, the following Eq. 7″ is used in place of Eq. 7 and the constants $C_1$ and $C_2$ for Eq. 5 are as follows:

$C_1 = 0.803$ $C_2 = 8.54 \times 10 - 5$ $$\begin{array}{rcl} t_E &=& t_P, \; Q_{IN} \leq 20 \\ &=& t_P - 215(1/20 - 1/Q_{IN}), \; Q_{IN} > 20 \end{array} \quad \text{(Eq. 7')}$$

VARIABLES INDEX

Symbols for Equations:

$C_1$, $C_2$ = constants in platelet collection efficiency equations $C_B$ = platelet concentration in collect bag, expressed as $10^3$ platelets/microliter $C_{PO}$ = donor postcount, expressed as $10^3$ platelets/microliter $C_{PR}$ = donor precount, expressed as $10^3$ platelets/microliter $E_C$ = platelet collection efficiency $f_{ACP}$ = AC expressed as a fraction of pure plasma volume $f_{BP}$ = fraction of $V_B$ processed in platelet collection procedure $f_{SP} = V_{CON}$ expressed as a fraction of $V_B$ $F_Y$ = user-specific (e.g., blood bank/center) yield calibration factor H = hematocrit of donor or patient I = AC infusion rate constant L = donor or patient height, inches P = plasma collect factor $Q_{Ac}$ = AC flow, ml/min $Q_{ACD}$ = AC flow infused into donor for platelet collection procedures, ml/min $Q_{IN}$ = inlet flow, ml/min $Q_{INA}$ = average inlet flow for platelet procedures, ml/min $Q_{INO} = R Q_{ACD}$ = inlet flow associated with $Q_{ACD}$, ml/min R = AC ratio $t_E$ = equivalent procedure time, min $t_P$ = procedure time, min $V_B$ = total blood volume of donor or patient, ml $V_C$ = volume of pure plasma in platelet collect bag, ml $V_{CB}$ = total volume in platelet collect bag, ml $V_{CON}$ = volume constraint for total pure plasma collected, ml $V_{CONH}$ = higher value of $V_{CON}$, ml $V_{CONL}$ = lower value of $V_{CON}$, ml $V_{SP}$ = volume of pure plasma in source plasma bag, ml $V_{SPB}$ = total volume in source plasma bag, ml W = donor or patient weight, lbs $W_C$ = weight constraint associated with $V_{CON}$, lb Y = platelet yield, number of platelets.

As noted above, the optimizer assembly 140 associated with principles of the present invention interfaces with or at least provides information to one or more blood component collection assemblies 10 to provide a blood component collection system 2. That is, although there are definite advantages to having an interface between the optimizer assembly 140, particularly the optimizer module 144, and the blood component collection device 18, the optimization procedure may be performed at any location and input into the blood component collection device 18 in any manner. Since the general principles of the blood component collection assembly 10 were described with relation to the collection assemblies 10, 10" which included the blood component collection device 18 and its various features, the optimizer assembly 140 will be described in relation to such assemblies 10', 10". However, it will be appreciated that the fundamental optimization principles of the present invention are not limited to these collection procedures and/or apparatus.

As noted (FIG. 1), the optimization assembly 140 generally includes a central input station 148, as well as an optimizer module 144 for each blood component collection device 18. Initially, it should be noted that the optimizer module 144 may be separate from the internal control of the blood component collection device 18 which is accessible by the operator interface module 16. However, typically the optimizer module 144 will be integrated with this internal control along with the above-described prediction model 20.

Figure 5:
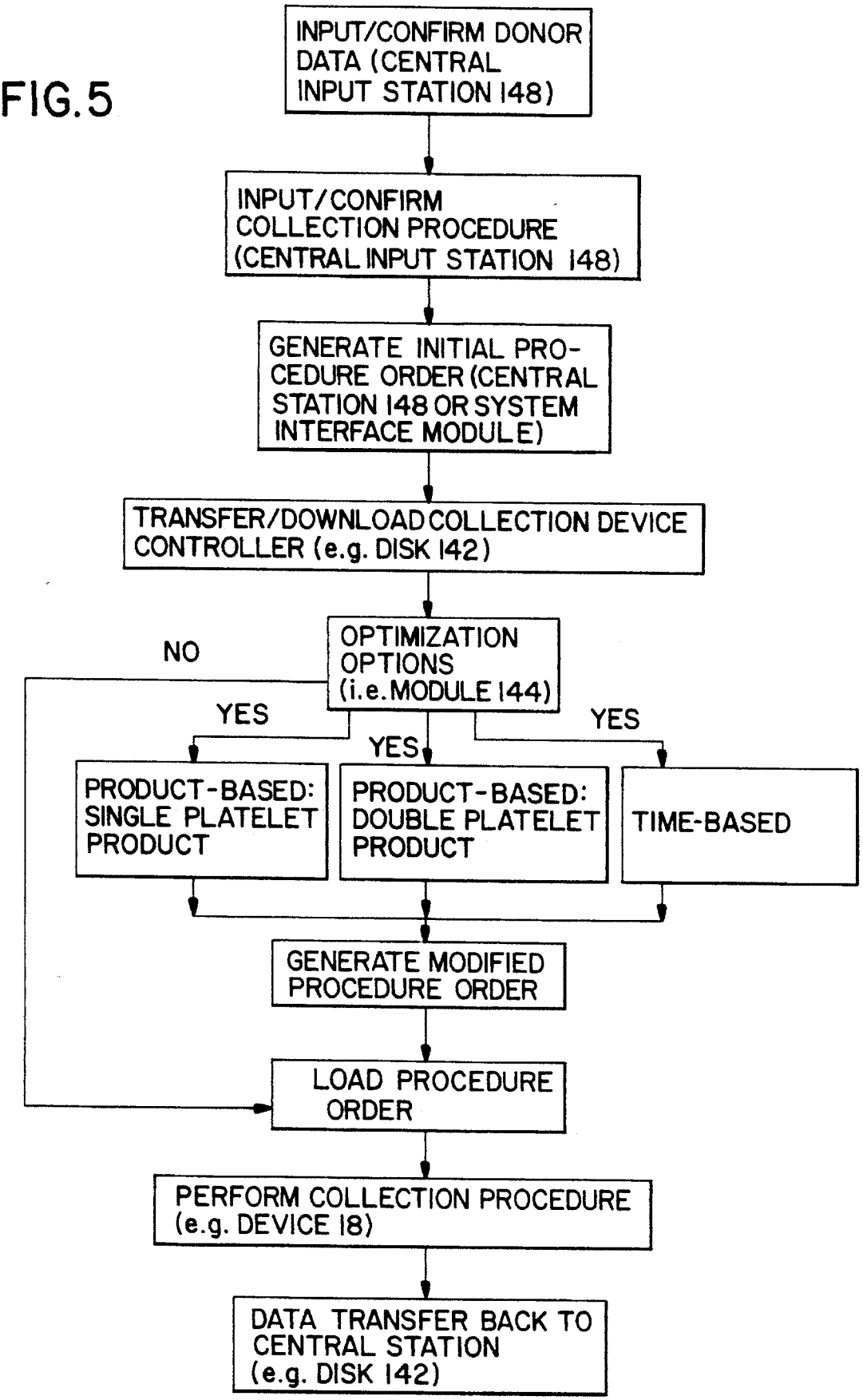
FIG. 5 is a flow chart of a blood component collection procedure utilizing principles of the present invention.

Referring to FIG. 5, the optimizer assembly 140 will be described with regard to a standard procedure. The central input station 148 will typically be used by blood banks/centers as the primary means for donor data input and donor data management. Information relating to a donor such as sex, height, weight, and demographics will be input at the central input station 148. Moreover, information relating to the donor's hematocrit and a blood component precount, both of which may be obtained from a donor blood sample and determined by known techniques such as cell counters, may also be entered at the central station 148. In addition to donor-related data, the particular type of collection procedure to be used for the donor (e.g., single needle or double needle) may be input/confirmed at the central input station 148. Based upon this information and certain site-standardized conditions (e.g., total procedure time, collection efficiency, AC infusion rate), an initial procedure order is thereafter generated which specifies the various process control parameters associated with the selected collection procedure.

The initial procedure order may be transferred/downloaded onto the internal control of a blood component collection device 18 by a computer disk 142 (FIG. 1) or electronically if a network system is implemented (not shown), through use of the operator interface module 16 if required/desired. When this operator interface module 16 exists, it may of course be used for the initial donor data input and/or to generate the initial procedure order and thereby alleviate the need for a central input station 148. However, it may be more efficient to use the central input station. Although this initial procedure order may be used in the collection process, the initial procedure order may be optimized in accordance with principles of the present invention to obtain one or more optimal values for the process control parameters. As noted, this optimization process may be utilized before the collection procedure is actually initiated, but may also be initiated during a given collection procedure and such is referred to as downstream optimization.

Figure 7:
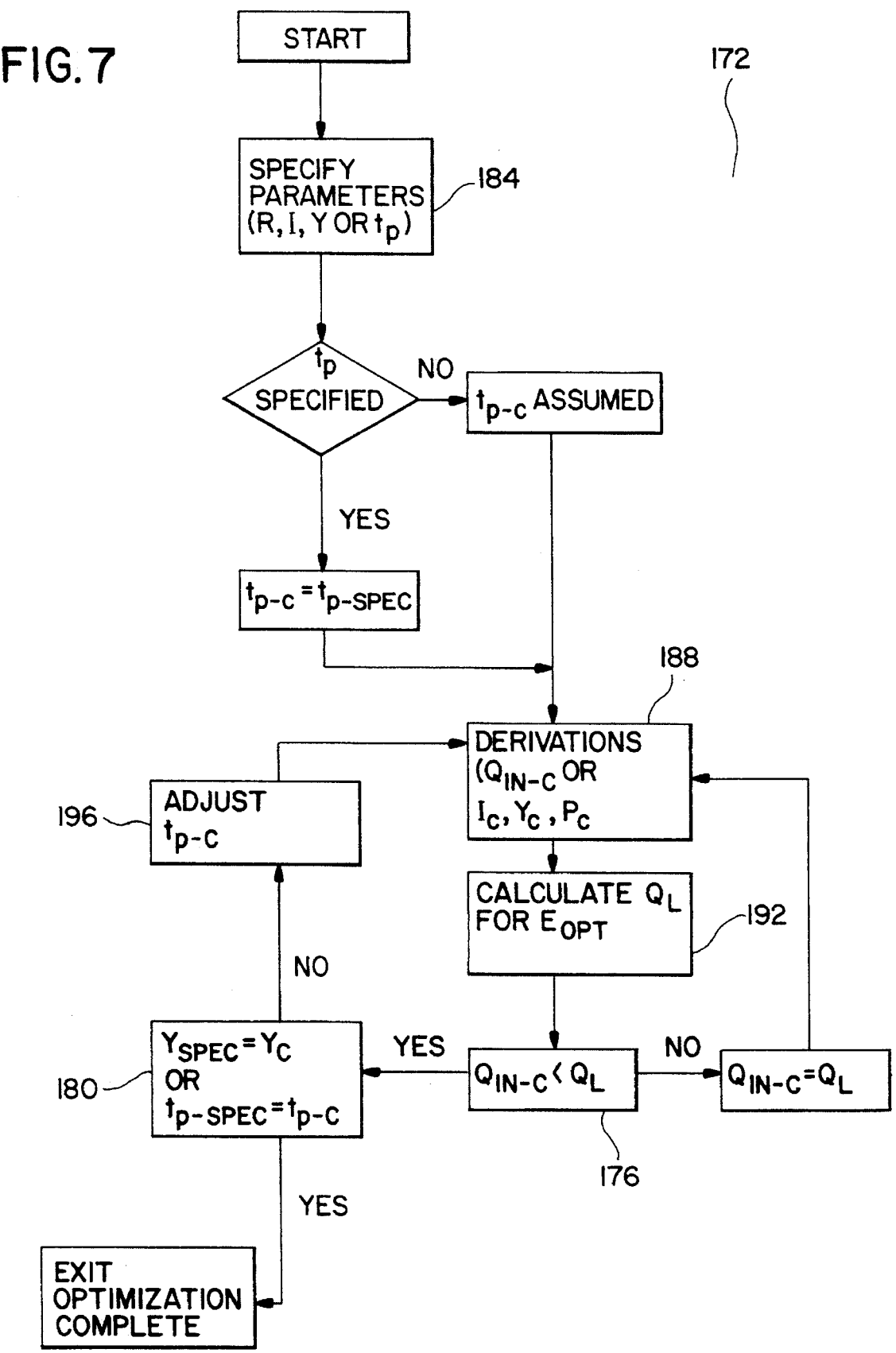
FIG. 7 is a flow chart of one optimization model for deriving at least one optimal process parameter from a desired blood component yield or from a total procedure time in accordance with principles of the present invention.

With regard to the various optimization options, process control parameters may be derived for a product-based optimization. More particularly, the optimizer assembly 140 and specifically the optimizer module 144 derives process control parameters for achieving a predetermined yield of blood components through a maximization of at least one process parameter as will be discussed below in relation to the optimization models 152 (FIG. 6), 172 (FIG. 7). As noted above, in the United States a single platelet product (SPP) is $3 \times 10^{11}$ platelets and a double platelet product (DPP) is $6 \times 10^{11}$ platelets. Consequently, the optimizer module 144 may be configured to provide a number of product-based optimizations such as SPP and DPP. Although the exact values for a current U.S. SPP and DPP could be configured into the optimizer module 144, in order to increase the probability that the actual yield will equal or exceed the yield requirements for a current U.S. SPP or a DPP, the site may configure a SPP to be $3.5 \times 10^{11}$ platelets and a DPP to be $7.0 \times 10^{11}$ platelets (e.g., to effectively provide a given confidence level that the specified yield will actually be met).

The optimizer module 144 may also be configured to provide a time-based optimization. That is, for a given amount of time which a donor is available, the optimizer module 144 will derive those process parameters which allow for the collection of a "maximum" amount of platelets in this time period in relation to a maximization of at least one of the process control parameters.

Once the optimization is complete, the values for the various process control parameters generated thereby, as well any ancillary/previously specified values, are downloaded to the internal control of the blood collection device 18 such that the collection procedure may be initiated or reinitiated (downstream optimization) as the case may be in accordance with these values. Once the procedure is completed, certain data is transferrable (via the disk 142 or electronically as noted) back to the central input station 148 for further use with regard to the particular donor. In addition, this information as well as the initial input may be used to generate various types of reports which may further assist in the management of the blood bank/center (e.g., individual run, donor/patient, summary reports). That is, this information may be used in the derivation of subsequent procedure orders for the particular donor. For instance, in the event that a certain AC infusion rate was used in the collection procedure which had certain effects on the donor, this may be recorded in the central input station 148 such that a lower AC infusion rate would be suggested/required for subsequent donations by the donor.

Figure 6:
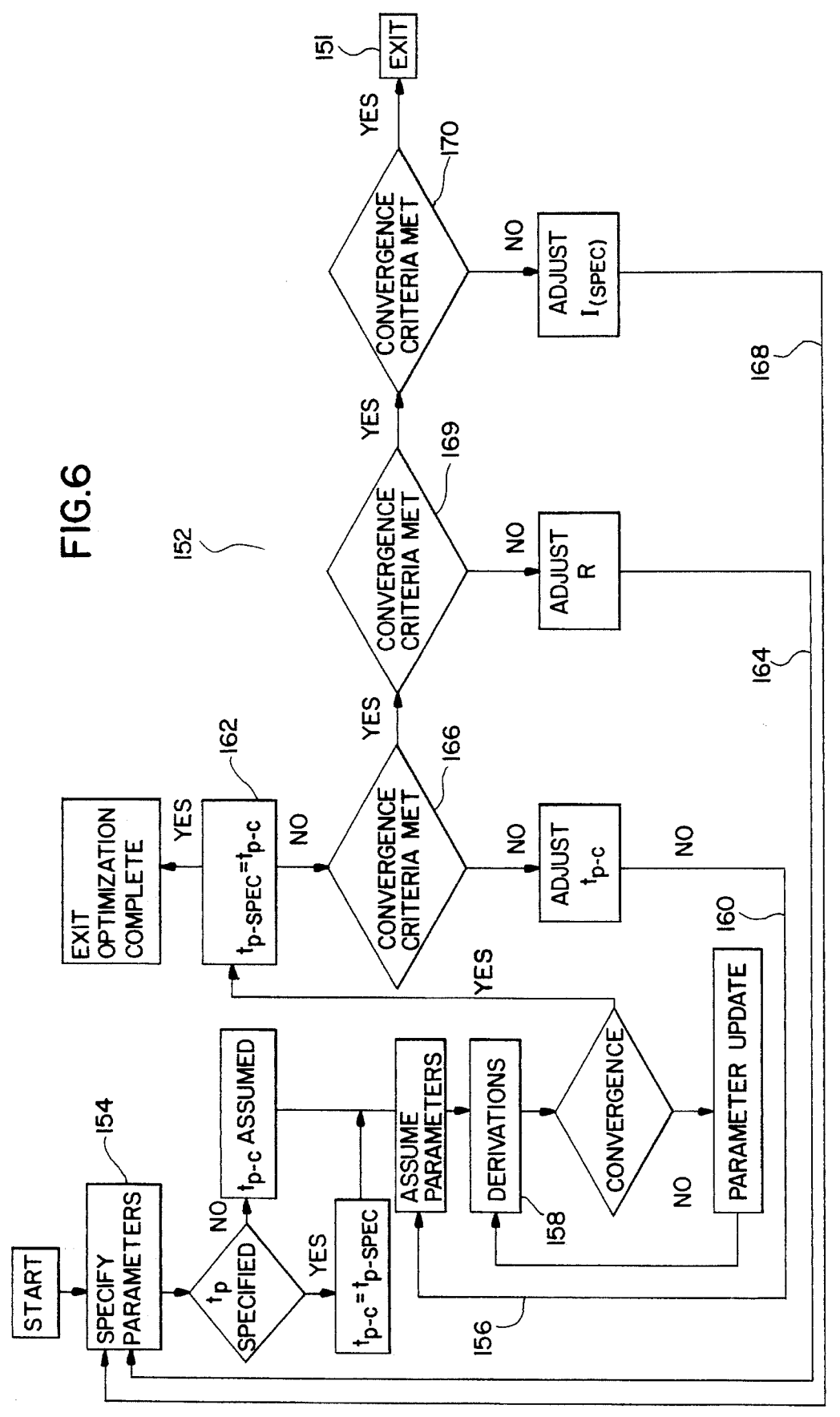

One model which may be incorporated into the optimization module 144 is illustrated in FIG. 6 and will be described with regard to platelet collections in accordance with the dual needle configuration of FIG. 2, although the module 144 may be used with a variety of other collection procedures and including the single needle configuration of FIG. 3, as well as with various other blood components. Initially, it should be noted that all references in FIG. 6 to "derivations" are actually provided by the prediction model 20 discussed above such that there is either an appropriate interface between the prediction model 20 and optimizer module 144 or the optimization module 144 actually includes the prediction model 20. Moreover, as noted the prediction model 20 is specific to the blood component collection device 18 and to platelet collections. Therefore, if other devices are used the associated prediction model would also likely change as noted. Moreover, the associated prediction model may also vary in the case where different blood components such as red blood cells are to be collected.

The optimizer model 152 of FIG. 6 may be used for both product-based and time-based optimizations. Initially, the optimizer model 152 will be described with regard to a product-based optimization. That is, the fundamental premise of the optimization is to achieve a predetermined platelet (or other blood component type) yield (or within a yield range), preferably in the minimum amount of time.

The optimizer model 152 of FIG. 6 is comprised of four iterative loops. Generally, the first loop 156 is a derivation of an inlet flow ($Q_{IN}$) associated with a specified AC infusion rate ($I_{SPEC}$) which is typically set at a maximum value for purposes of the present invention and which is entered at the input station 154. This derivation is thereafter performed by the processing station 158 and includes the solution of Eqs. 4, 8, 14, and 16 and/or equations ancillary thereto by the prediction model 20 as discussed above.

There are of course various convergence criterion/criteria which may be incorporated into the first loop 156. For instance, convergence may be based upon the current inlet flow ($Q_{IN-C}$) in the first loop 156 through use of a binary search technique. In this case, in solving the noted equations at the processing station 158 certain parameters remain fixed in the iterative derivation of the inlet flow ($Q_{IN}$) which achieves the specified AC infusion rate ($I_{SPEC}$) and these parameters are also specified at input station 154. These include the total blood volume ($V_B$) which can be calculated using Eq. 10 since the donor's height, weight, and sex are entered at the central input station 148, and the AC ratio (R), which can be calculated using Eq. 9 since the donor's hematocrit (H) has been determined, or may be specified at some value. Moreover, the total procedure time ($t_P$) remains fixed in each iterative derivation of the inlet flow ($Q_{IN}$) associated with the specified AC infusion rate ($I_{SPEC}$) in the first loop 156. However, since the total procedure time ($t_P$) is not known in the case of a product-based optimization and thus cannot be specified at the input station 154, a current total procedure time ($t_{P-C}$) initially will be assumed (e.g., this assumption is configured in the optimizer model 152 and since a range of total procedure times is provided in the prediction model 20 as noted above, the mean total procedure time ($t_P$) is typically configured into this portion of the optimizer model 152 as the initial current total procedure time ($t_{P-C}$)). The "current" designation is used for the total procedure time in this case since the optimizer model 152 provides for an adjustment of the total procedure time after each iterative determination of the inlet flow ($Q_{IN}$) which provides the specified AC infusion rate ($I_{SPEC}$) in the second loop 160 in order to achieve the desired yield (Y) if required in the case of a product-based optimization as will be discussed in more detail below.

Generally, the inlet flow-based binary search technique convergence may be provided by assuming a current value for the inlet flow ($Q_{IN-C}$), calculating a current plasma collect factor ($P_C$) using the current total procedure time ($t_{P-C}$), calculating a current AC infusion rate ($I_C$) using the current inlet flow ($Q_{IN-C}$) and current plasma collect factor ($P_C$), and adjusting the current inlet flow ($Q_{IN-C}$) (at the parameter update in the first loop 156) in accordance with the selected binary search technique until there is a predetermined convergence between the two most recent values for the current inlet flow ($Q_{IN-C}$) (i.e., wherein the difference between the two most recent values of $Q_{IN-C}$ is less than some predetermined amount which means that the convergence criterion is met). In the case of a binary search technique, there will always be convergence (i.e., the convergence criterion will always be met) such that the optimizer model 152 will always exit the first loop 156 and enter the second loop 160.

As an alternative to the noted inlet flow-based convergence criterion/criteria and the noted binary search technique, another possibility is to base convergence on the specified AC infusion rate ($I_{SPEC}$) and use an iterative derivation to determine the desired inlet flow ($Q_{IN}$). In this case, the first loop 156 is used to once again iteratively derive the inlet flow ($Q_{IN}$) which provides the specified AC infusion rate ($I_{SPEC}$) at the processing station 158 from certain specified parameters. That is, the first loop 156 is still a maximization of the inlet flow ($Q_{IN}$) based upon the specified AC infusion rate ($I_{SPEC}$) which should be associated with the donor 14. This is again primarily through the solution of Eqs. 4, 8, 14, and 16 and/or equations ancillary thereto by the prediction model 20 discussed above.

For purposes of solving the above-identified equations in relation to the infusion rate-based convergence criterion, certain parameters remain fixed in the iterative derivation of the inlet flow ($Q_{IN}$) which achieves the specified AC infusion rate ($I_{SPEC}$) in the first loop 156 and these parameters are also specified at the input station 154. These include the specified AC infusion rate ($I_{SPEC}$) which is known and which is typically a maximum value for the donor 14, the total blood volume ($V_B$) which can be calculated using Eq. 10 since the donor's 14 height, weight, and sex are entered in the central input station 148, and the AC ratio (R) which can be calculated using Eq. 9 since the donor's 14 hematocrit (H) has been determined and in accordance with the above (e.g., via direct analysis with a cell counter), and is thereafter in the central input station 148, or may be entered as modified input data. Moreover, the total procedure time ($t_P$) remains fixed in each iterative derivation of the inlet flow ($Q_{IN}$) associated with the specified AC infusion rate ($I_{SPEC}$). However, once again the total procedure time ($t_P$) is not known in the case of a product-based optimization and thus cannot be specified at the input station 154. Therefore, a current total procedure time ($t_{P-C}$) initially will be assumed (e.g., this assumption is configured in the optimizer model 152, and since a range of total procedure times is provided in the prediction model 20 as noted above, the mean total procedure time ($t_P$) is typically configured into the first loop 156 of the optimizer model 152). The "current" designation for the total procedure time is used for the above-identified reasons relating to the adjustment of the total procedure time in the second loop 160 if required to attain the desired yield (Y).

The solution of Eqs. 4, 8, 14, and 16 also requires that certain values be assumed for certain of the remaining parameters with still other parameters being derived from this assumption. In this case, an iterative procedure is used and updated/current values are used in the next iterative calculation(s). All parameters which change on each iteration of the first loop 156 are identified herein with a "c" subscript to designate that the most current value is to be used. Although the derivation of that inlet flow ($Q_{IN}$) which provides the specified AC infusion rate ($I_{SPEC}$) may be accomplished in a variety of manners via Eqs. 4, 8, 14, and 16, one way is to assume a current value for the plasma collect factor ($P_C$), then calculate the current inlet flow ($Q_{IN-C}$) using the specified AC infusion rate ($I_{SPEC}$), then calculate the current yield ($Y_C$), then calculate the current plasma collection factor ($P_C$) using the current yield ($Y_C$), and repeat this procedure with the current values until there has been acceptable convergence on the current inlet flow ($Q_{IN-C}$) in relation to the specified AC infusion rate ($I_{SPEC}$) (e.g., when the particular convergence criterion/criteria is met/established). When there is acceptable infusion rate-based convergence, the optimizer model 152 exits the first loop 156 and enters the second loop 160. In order to offer protection for cases when there is no such convergence, a maximum number of iterations for the first loop 156 may be specified (not shown).

The second loop 160 of the optimizer model 152 is a total procedure time ($t_P$) iteration. That is, the second loop 160 is an iterative adjustment of the current total procedure time ($t_{P-C}$). Initially, in the second loop 160 and in the case of a product-based optimization the model 152 will never exit at the first comparator 162 since a total procedure time ($t_P$) is not specified at the input station 154. Consequently, the optimizer model 152 proceeds to the second comparator 166 where convergence criteria (i.e., more than one check) is made. One convergence criterion which is checked at the second comparator 166 is whether the current yield ($Y_C$) is greater than or equal to the desired and specified yield (Y). In this case, the current yield ($Y_C$) may be calculated based upon the values specified at the input station 158, values derived at the processing station 158, and the current total procedure time ($t_{P-C}$) for comparison with the desired and specified yield (Y) (in some cases, this current yield calculation ($Y_C$) may have been performed in the first loop 156 and need not be repeated in the second loop 160). If the yield convergence criterion is met, the model 152 exits the second loop 160 and actually exits all the way through to the exit 151, as will be discussed below. In this case, the specified/derived values are "optimal" and the collection procedure could be performed on the device 18 using the noted values for the various control parameters.

In the event that the yield-based criterion is not met at second comparator 166, the second comparator 166 looks to a total procedure time-based convergence criterion which may be similar to that discussed above with regard to the inlet flow-based criterion (e.g., using a binary search technique with the convergence criterion then being a predetermined difference between the two most current values of the total procedure time ($t_{P-C}$)). On the first time through the second loop 160 after the noted yield-based convergence criterion has failed and the total procedure time convergence criterion has failed, the current total procedure time ($t_{P-C}$) is adjusted and the model 152 returns to the first loop 156. That is, each time that the current total procedure time ($t_{P-C}$) is adjusted in the second loop 160, the entirety of the first loop 152 is repeated (i.e., a new inlet flow ($Q_{IN}$) associated with the specified AC infusion rate ($I_{SPEC}$) is derived using the current total procedure time ($t_{P-C}$) provided by the adjustment in the second loop 160). Other convergence criterion/criteria could be used in the second loop 160, such as specifying a maximum number of iterations to be performed by the second loop 160.

In the event that the yield-based convergence criterion is not met on the second loop 160 and the total procedure time-based convergence criterion is met at the second comparator 166 in the second loop 160, the optimizer model 152 exits the second loop 160 and enters the third loop 164. The third loop 164 is an iterative adjustment of the AC ratio (R). However, the model 152 initially enters the third comparator 169 where convergence criteria (i.e., more than one) are checked. One convergence criterion is again the above-noted yield-based convergence criterion. If this yield-based convergence criterion is again not met, an AC ratio-based convergence criterion is checked at the third comparator 169. This may be similar to the inlet flow-based criterion discussed above (e.g., using a binary search technique with the convergence criterion being the two most current values of the AC ratio). On the first time through the third loop 164 after the yield-based criterion has failed and the AC ratio-based convergence criterion has failed, the AC ratio is adjusted and the optimizer model 152 returns to the first loop 152. That is, each time that the AC ratio (R) is adjusted in the third loop 164, the entirety of the first and second loops 156, 160, respectively, is repeated. Other convergence criterion/criteria could be used in the third loop 164, such as specifying a maximum number of iterations of the third loop 164.

In the event that the yield-based convergence criterion is not met in the second or third loops 160, 164, respectively, and the second and third comparator 166, 169, respectively, and the AC ratio-based convergence criterion is met at the third comparator 169 in the third loop 164, the optimizer model 152 exits the third loop 164 and enters the fourth loop 168. The fourth loop 168 is an iterative adjustment of the specified AC infusion rate ($I_{SPEC}$). However, the optimizer model 152 initially enters the fourth comparator 170 where convergence criteria (i.e., more than one) are checked. One convergence criterion is the noted yield-based convergence criterion. If the noted yield-based convergence criterion is not met at the fourth comparator 170, an AC infusion rate-based criterion is checked at the fourth comparator 170. This may be similar to the inlet-flow based criterion discussed above (e.g., using a binary search technique with the convergence criterion being the two most current values of the AC infusion rate). On the first time through the fourth loop 168 after the yield-based criterion has failed and the AC infusion rate-based convergence criterion has failed, the AC infusion rate is adjusted and the model 152 returns to the first loop 152. That is, each time that the specified AC infusion rate ($I_{SPEC}$) is adjusted, the entirety of the first, second and third loops 156, 160, 164, respectively, is repeated (with the AC ratio set back to its initial value as entered at the input station 154 on each iteration of the fourth loop 168). Other convergence criterion/criteria could be used in the fourth loop 168, such as specifying a maximum number of iterations of the fourth loop 168. In cases where the specified AC infusion rate ($I_{SPEC}$) is actually the maximum AC infusion rate, typically the fourth loop 168 will execute only a single time with a one-time increase in the AC infusion rate of, for instance, 20% (e.g., may be site-configured).

In the foregoing loops where a yield-based convergence criteria are identified, when the criteria are met the optimizer model 152 exits to exit 151 and the specified/derived (i.e., current) values for the various process control parameters may be provided to the device 18 for performing the collection procedure. However, there may be cases where no optimization occurs, such as when the optimizer model 152 exits to the exit 151 based upon the AC infusion rate based convergence criterion being met.

The optimizer model 152 may also be used for a time optimization. That is, the optimizer model will derive optimal process parameters for a predetermined total procedure time ($t_P$) through maximization of at least one of the process parameters in order to maximize the platelet collection (or for other blood component types). In this case, the optimizer model 152 only executes the first loop 156 to derive the inlet flow ($Q_{IN}$) associated with a specified AC infusion rate ($I_{SPEC}$) (typically a maximum value) using the input total procedure time ($t_P$) in this iterative derivation instead of the assumed total procedure time ($t_P$) referenced above. Once there is acceptable convergence as defined above in the product-based optimization such that model 152 exits the first loop 156, the current yield ($Y_C$) may be calculated in the first loop 156 (but again may already have been calculated in the first loop 156 at the processing station 158 such that no further calculation is required) and the convergence criterion will be met at the first comparator 162 when entering the second loop 160 (i.e., in a time-based optimization when a total procedure time is specified at the input station 154, the model 152 will exit when entering the second loop 158). As a result, the inlet flow ($Q_{IN}$) and AC infusion rate (I) will be optimal and the collection procedure may be performed with such values.

Figure 8:
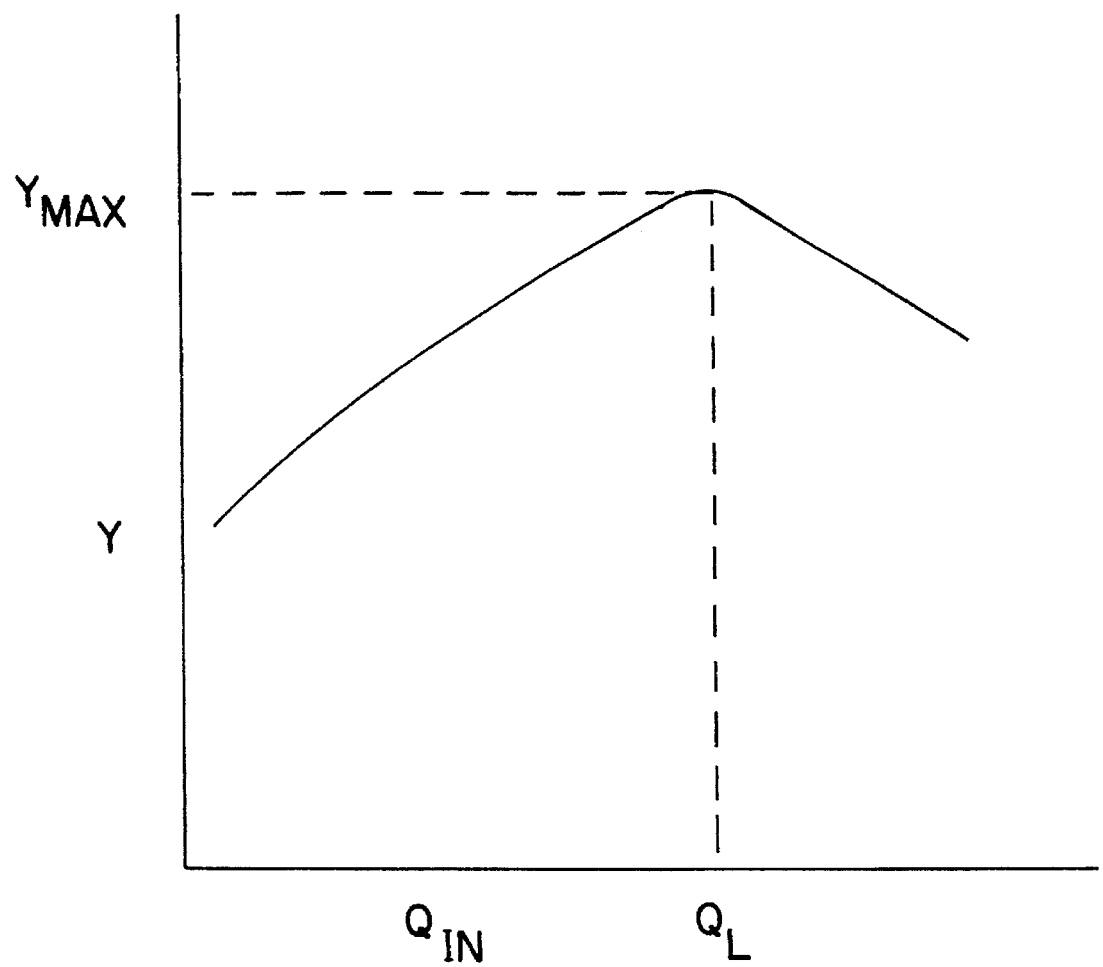
FIG. 8 is a yield/inlet flow curve.

Another optimization model is presented in FIG. 7 and may be used for both product-based and time-based optimizations. As in the case of the optimizer model 152, the optimizer model 172 may interface with the prediction model 20 or actually integrally incorporate the prediction model 20, and thus reference to Eqs. 1–22 will be further made herein. Generally, the optimizer model 172 is based upon the principle that optimization occurs when an optimal inlet flow ($Q_L$) associated with an optimum system collection efficiency is used in the derivation of various process control parameters. Referring to FIG. 8, a representative inlet flow ($Q_{IN}$)/Yield (Y) curve is presented to show the optimal inlet flow ($Q_L$) associated with the maximum yield ($Y_{MAX}$). This optimal inlet flow ($Q_L$) is mathematically expressed by Eq. 23 presented below which results from differentiating Eq. 4 of the prediction model 20 with regard to the inlet flow ($Q_{IN}$). As can be appreciated, where different algorithms are used in the associated prediction model (whether based upon collection of blood components other than platelets, different collection apparatus, or alternative derivations of the various parameters with the same collection procedure and apparatus), the optimal inlet flow may be mathematically expressed in a different manner.

$$Q_L = \left( \frac{C_1}{2C_2} \right) e^{-9.91(1-1/R)H} - C_3 \quad \text{(Eq. 23)}$$

$$C_3 = \frac{1}{2(t_P/K_7 - 1/K_9)}, \quad \begin{array}{l} Q_o \geq 45 \text{ for Dual Needle ("DN")} \\ \geq 20 \text{ for Single Needle ("SN")} \end{array} \quad \text{(Eq. 24)}$$

$$= 0, \quad \begin{array}{l} Q_o < 45 \text{ for DN} \\ < 20 \text{ for SN} \end{array} \quad \text{(Eq. 25)}$$

| | | | | |
|---|---|---|---|---|
| $K_7$ | = | 500 (DN) | $K_9$ = 45 (DN) | (Eq. 26) |
| | = | 215 (SN) | = 20 (SN) | |
| $C_1$ | = | 0.803 (SN, DN without stepdown) | | (Eq. 27) |
| | = | 0.840 (DN with stepdown) | | |
| $C_2$ | = | $4.08 \times 10^{-5}$ (DN) | | (Eq. 28) |
| | = | $8.54 \times 10^{-5}$ (SN) | | |

Based upon the foregoing, the optimal inlet flow ($Q_L$) is really "optimal" in terms of the collection apparatus.

Referring again to FIG. 7, the optimizer model 172 will initially be described with regard to a product-based optimization wherein the desired yield (Y) is specified at input station 184. Generally, the inlet flow ($Q_{IN}$) associated with a specified AC infusion rate ($I_{SPEC}$) (typically the maximum AC infusion rate and also specified at input station 184) is iteratively derived from certain other specified parameters. This inlet flow calculation, particularly when the maximum AC infusion rate ($I_{MAX}$) and maximum AC ratio ($R_{MAX}$) are specified, the inlet flow ($Q_{IN}$) is optimal based on the physiological considerations of the donor 14. This is primarily through the solution of Eqs. 4, 8, 14, and 16 and/or equations ancillary thereto by the prediction model 20 discussed above. For purposes of solving these equations certain parameters remain fixed in the iterative derivation of the inlet flow ($Q_{IN}$) which achieves the specified AC infusion rate ($I_{SPEC}$) and these parameters are also specified at input station 184. These include the total blood volume ($V_B$) which can be calculated using Eq. 10 since the donor's height, weight, and sex are entered in the central input station 148, and the AC ratio (R), which can be calculated using Eq. 9 since the donor's hematocrit (H) has been determined, or may be specified at some maximum value. Moreover, the total procedure time ($t_P$) remains fixed in each iterative derivation of the inlet flow ($Q_{IN}$) associated with the specified AC infusion rate ($I_{SPEC}$). However, since the total procedure time ($t_P$) is not known in the case of a product-based optimization and thus cannot be specified at the input station 184, a current total procedure time ($t_{P-C}$) initially will be assumed (e.g., this assumption is configured in the optimizer model 172 and since a range of total procedure times is provided in the prediction model 20 as noted above, the mean total procedure time ($t_P$) is typically configured into this portion of the optimizer model 172 as the initial current total procedure time ($t_{P-C}$)). The "current" designation is used for the total procedure time in this case since the optimizer model 172 provides for an adjustment of the total procedure time after each iterative determination of the inlet flow ($Q_{IN}$) which provides the specified AC infusion rate ($I_{SPEC}$) in order to achieve the desired yield (Y) if required in the case of a product-based optimization as will be discussed in more detail below.

The solution of Eqs. 4, 8, 14, and 16 also requires that certain values initially be assumed for certain of the remaining parameters. In this case, an iterative procedure is used in the solution of the yield equation (Eq. 4) (and including equations ancillary thereto as noted above) and updated values are used in the next iterative calculation(s) at the processing station 188. Although the derivation of that inlet flow ($Q_{IN}$) which provides the specified (typically maximum) AC infusion rate ($I_{SPEC}$) may be accomplished in a variety of manners via Eqs. 4, 8, 14, and 16, one way is to assume a current value for the plasma collect factor (P), then calculate the current inlet flow ($Q_{IN-C}$) using the specified AC infusion rate ($I_{SPEC}$), then calculate the current yield ($Y_C$), then calculate the current plasma collection factor ($P_C$) using the current yield ($Y_C$), and repeat the foregoing with the updated parameters, all within the processing station 188, until there has been acceptable convergence on the current inlet flow ($Q_{IN-C}$) in relation to the specified AC infusion rate ($I_{SPEC}$).

In addition to the calculation of the current inlet flow ($Q_{IN-C}$) associated with the specified AC infusion rate ($I_{SPEC}$), the above-discussed optimal inlet flow ($Q_L$) is calculated at processing station 192. Consequently, a comparison can be made between the current inlet flow ($Q_{IN-C}$) which was derived in the above-described manner and the optimal inlet flow ($Q_L$) at the first comparator 176. If the current inlet flow ($Q_{IN-C}$) is less than the optimal inlet flow ($Q_L$) at the first comparator 176, the specified values for the various parameters associated with the inlet flow $Q_{IN}$ are "optimum", namely the AC ratio (R) and the AC infusion rate (I) specified at the input station 184. Thereafter, the current yield ($Y_C$) (which was calculated in the derivation of the current inlet flow ($Q_{IN-C}$) associated with the specified AC infusion rate ($I_{SPEC}$) at the processing station 188) is compared with the input yield (Y) at second comparator 180. In the event that there has been acceptable convergence between these yield values, the current total procedure time ($t_{P-C}$) is also "optimal". However, in the event that there has not been acceptable convergence between these yield values, the current total procedure time ($t_{P-C}$) is adjusted at adjusting station 196 and the foregoing iterative derivation of the current inlet flow ($Q_{IN-C}$) associated with the specified AC infusion rate ($I_{SPEC}$) is repeated until such convergence is achieved (i.e., using the initially specified AC infusion rate ($I_{SPEC}$) and the now adjusted current total procedure time ($t_{P-C}$, a new current inlet flow ($Q_{IN-C}$) is iteratively derived in the above-described manner).

Referring back to the first comparator 176, if the current inlet flow ($Q_{IN-C}$) associated with the specified AC infusion rate ($I_{SPEC}$) derived at processing station 188 is greater than the optimal inlet flow ($Q_L$), a current AC infusion rate ($I_C$) associated with this particular inlet flow ($Q_L$) is iteratively derived at the processing station 188 generally in the above-described manner (i.e., the initially specified AC infusion rate ($I_{SPEC}$) is disregarded in this derivation and a current AC infusion rate ($I_C$) is iteratively derived to coincide with the inlet flow ($Q_L$)). In this case, the current inlet flow ($Q_{IN-C}$) will always be equal to the optimal inlet flow ($Q_L$) at the first comparator 176 and the optimizer model 172 thereafter proceeds to the second comparator 180 for the yield comparison in accordance with the above-described procedure.

The optimizer model 176 may also be used for a time-based optimization. In this case, the total procedure time ($t_P$) is specified at the input station 184 as a specified total procedure time ($t_{P-SPEC}$) and thus is not assumed as in the product-based optimization. The optimizer model 172 thereafter proceeds in the same manner discussed above with regard to the product-based optimization except at the second comparator 180. Since no yield was input there is no yield comparison made at the second comparator 180. Instead a total procedure time comparison is made at the second comparator 180. Since the current total procedure time ($t_{P-C}$) was set equal to the specified total procedure time ($t_{P-SPEC}$) prior to the model 172 proceeding to the processing station 188 in this time-based optimization, the model 172 will exit each time at the second comparator for a time-based optimization.

In addition to the above-described product-based and time-based optimizations, the principles of the present invention may be extended to other applications relating to enhancing blood component system management. For instance, an optimization in accordance with principles of the present invention may be extended to encompass donor management issues. In one such case, another "optimization" associated with the blood component collection process would be to collect blood components as dictated by existing inventory (i.e., use optimization as dictated by existing inventory (i.e., use optimization as an inventory control). That is, information relating to the inventory of the various types of blood components in the blood bank/center and/or the demand for one or more blood component types could be maintained such that specific collection procedures could be selected to accommodate for a low supply of a given blood component type and/or a high demand for such blood component type. More specifically, in the event that the supply of red blood cells was low and/or the demand for red blood cells was high, or anticipated to be so in the near future, prompts could be provided to operators that red blood cells should be selected for collection if possible from donors during a given time period. Relatedly, the optimization principles of the present invention would be applicable to maintaining data on blood component collections from a given donor such that a determination could be made as to what type or types of blood components from the particular donor provided the maximum yield in the collection procedure. That is, information could be collected and maintained from prior blood component donations such that a determination could be made for a specific donor as to which type or types of blood components the donor has had a propensity to produce maximum yields therefor.

Notwithstanding the foregoing description of the present invention in relation to an on-line blood component collection process, those skilled in the art will appreciate that the source of blood may be provided to the blood component collection device from an appropriate blood container (not shown) interconnected with the blood component collection device 18 versus receiving such directly from the donor. Moreover, the blood of course may be provided from alternative sources such as animals. Furthermore, as illustrated in FIG. 3 the described platelet harvesting procedure may be performed utilizing a single needle configuration. In addition, the present invention is applicable to the collection of other types of blood components such as red blood cells, white blood cells, and/or plasma, and is further applicable to the simultaneous collection of more than one blood component type. In the case of red blood cell collection and optimization in accordance with principles of the present invention, the donor's blood type should be known and used in various algorithms. Moreover, the present invention is not limited to the source being whole blood. That is, the principles of the present invention may be applicable to removal of a component from any liquid.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention, and such other embodiments, and with various modifications required by the particular applications or uses of the present invention. It is intended that the appended claims be construed to include alternative embodiments to the extent permitted by the prior art.

What is claimed is:

1. A method for collecting at least one predetermined type of blood component from a source of whole blood using a blood component collection system comprising a blood component collection device and collection procedure, said collection procedure having a plurality of parameters associated therewith, said method comprising the steps of:

providing biological data relating to a source of whole blood, said source being a human donor and said data comprising at least one of said donor's hematocrit, height, weight, and sex;

identifying a desired yield of at least one predetermined type of blood component;

associating a magnitude with each of a plurality of parameters associated with a collection procedure to be performed on said whole blood using a blood component collection system comprising a blood component collection device and said collection procedure, said associating step comprising performing a first deriving step comprising deriving a magnitude for at least one of said parameters from said providing and identifying steps;

inputting said magnitude of each said parameter into said blood component collection system after said associating step; and performing said collection procedure on said blood component collection device using said inputting step to collect said desired yield of said at least one predetermined type of blood component from said source of whole blood.

2. A method, as claimed in claim 1, wherein:

said biological data comprises said donor's hematocrit, height, weight, and sex.

3. A method, as claimed in claim 1, wherein:

one of said parameters is an inlet flow to said blood collection device and another of said parameters is a flow of anticoagulant into said blood component collection system, wherein said inlet flow comprises a flow of whole blood from said source and said flow of anticoagulant, wherein said source of said blood has a volume, wherein an AC ratio is a ratio of said inlet flow to said flow of anticoagulant, and wherein an AC infusion rate is a flow of said anticoagulant provided to said source per said volume of said source.

4. A method, as claimed in claim 3, wherein said performing a first deriving step further comprises:

deriving said magnitude of said inlet flow associated with a predetermined magnitude of said AC infusion rate.

5. A method, as claimed in claim 4, wherein said deriving said magnitude of said inlet flow step comprises:

using said predetermined magnitude of said AC infusion rate and a current magnitude for a total procedure time, said total procedure time being another of said parameters.

6. A method as claimed in claim 5, wherein said deriving said magnitude of said inlet flow step further comprises:

assuming a current magnitude for said inlet flow and performing a first iteration procedure comprising calculating a current magnitude for said AC infusion rate from at least said current magnitude of said inlet flow, evaluating convergence criteria relating to said current magnitude of said inlet flow, and adjusting said current magnitude of said inlet flow, repeating said first iteration procedure until at least one of first and second conditions is satisfied, said first condition being that said convergence criteria is established and said second condition being that said first iteration procedure has been performed a predetermined number of times.

7. A method as claimed in claim 6, wherein:

said deriving said magnitude of said inlet flow step comprises deriving a current magnitude for said AC infusion rate, said performing a first deriving step further comprising performing a second iteration procedure after said at least one of said first and second conditions is satisfied, said second iteration procedure step comprising calculating a current yield from said current magnitude of said inlet flow, said current magnitude of said AC infusion rate, and said current magnitude of said procedure time, comparing said current yield with said desired yield, performing said inputting step after said comparing step when said current yield is within a predetermined amount of said desired yield, adjusting said current magnitude of said total procedure time when said current yield differs from desired yield by more than said predetermined amount, repeating said deriving a magnitude of said inlet flow step after said adjusting said current magnitude of said total procedure time step, and repeating said second iteration procedure step after said repeating said deriving a magnitude of said inlet flow step until at least one of third and fourth conditions is satisfied, said third condition being that predetermined convergence criteria relating to said current total procedure time is established and said fourth condition being that said second iteration procedure step has been performed a predetermined number of times.

8. A method, as claimed in claim 7, wherein:

said performing a first deriving step further comprises performing a third iteration procedure after said second iteration procedure step and when said at least one of said third and fourth conditions is satisfied, said third iteration procedure step comprising adjusting said magnitude of said AC ratio, repeating said first and second iteration procedure steps, and repeating said third iteration procedure step until at least one of fifth and sixth conditions is satisfied, said fifth condition being that predetermined convergence criteria relating to said magnitude of said AC ratio is established and said sixth condition being that said third iteration procedure step has been performed a predetermined number of times.

9. A method, as claimed in claim 8, wherein:

said predetermined magnitude of said AC infusion rate is increased by a predetermined amount when at least one of said fifth and sixth conditions associated with said third iteration procedure step is satisfied, wherein said performing a first deriving step further comprises repeating said first, second, and third iteration procedure steps using said increased AC infusion rate.

10. A method, as claimed in claim 5, wherein:

said deriving said magnitude of said inlet flow step comprises deriving a current magnitude for said AC infusion rate, said performing a first deriving step further comprising iteratively calculating a current blood component yield using at least said current magnitude of said inlet flow and said current magnitude of said AC infusion rate and by using said providing step and by iteratively adjusting said magnitude of said current total procedure time until achieving at least one of first and second conditions, said first condition being within a predetermined variance of said desired yield of blood components and said second condition being performing said iteratively adjusting step a predetermined number of times.

11. A method, as claimed in claim 5, wherein said performing a first deriving step further comprises deriving a total procedure time, after said deriving said magnitude of said inlet flow step, which provides a current yield within a predetermined amount of said desired yield.

12. A method, as claimed in claim 3, wherein:

said associating step comprises selecting a maximum magnitude for said AC infusion rate, and wherein said associating step further comprises generating a calculated magnitude of said inlet flow using at least said maximum magnitude of said AC infusion rate.

13. A method, as claimed in claim 12, wherein said performing a first deriving step further comprises:

calculating a theoretical magnitude of said inlet flow which provides a maximum yield of said at least one predetermined blood component and comparing said theoretical and calculated magnitudes of said inlet flow, and wherein said inputting step comprises inputting the lesser of said theoretical magnitude and said calculated magnitude of said inlet flow.

14. A method, as claimed in claim 13, wherein:

another of said parameters is a total procedure time, wherein a current magnitude for said total procedure time is assumed, and wherein said performing a first deriving step further comprises performing a first iteration procedure, said performing a first iteration procedure step comprising calculating a current blood component yield using the lesser of said calculated and theoretical magnitudes of said inlet flow of whole blood, said current magnitude of said total procedure time, and said maximum AC infusion rate, comparing said current blood component yield with said desired blood component yield, and repeating said first iteration procedure step using an adjusted current total procedure time until at least one of first and second conditions is satisfied, said first condition being that said current magnitude of said blood component yield is within a predetermined amount of said desired blood component yield and said second condition being that said performing a first iteration procedure step has been performed a predetermined number of times.

15. A method as claimed in claim 13, wherein:

another of said parameters is a total procedure time and said performing a first deriving step further comprises assuming a current magnitude for said total procedure time and performing a first iteration procedure, said performing a first iteration procedure step comprising calculating a current yield from the lesser of said actual and theoretical magnitudes of said inlet flows, a maximum magnitude for said AC ratio, said maximum magnitude of said AC infusion rate, and said current magnitude of said procedure time, comparing said current yield with said desired yield, incrementally adjusting said current magnitude of said total procedure time when said current yield differs from desired yield by more than a predetermined amount, and repeating said first iteration procedure step until at least one of a first and second condition is satisfied, said first condition being that said current yield is within said first predetermined amount of said desired yield and said second condition being that said first iteration procedure step has been performed a predetermined number of times.

16. A method, as claimed in claim 3, wherein:

said at least one of said parameters is a total procedure time, said performing a first deriving step comprising maximizing said inlet flow and minimizing said total procedure time.

17. A method, as claimed in claim 1, further comprising the steps of:

providing a magnitude for each of said parameters before said identifying step;

performing said collection procedure on said blood component collection device before said identifying step, using said providing a magnitude step, and for a first time period, wherein said associating step is performed after expiration of said first time period.

18. A method, as claimed in claim 1, wherein:

one of said parameters is a total procedure time, and wherein said performing a first deriving step comprises minimizing said magnitude of said total procedure time based upon said magnitude of at least one of said parameters other than said total procedure time.

19. A method, as claimed in claim 18, wherein:

one of said parameters is an inlet flow to said blood collection device and another of said parameters is a flow of anticoagulant into said blood component collection system, wherein said inlet flow comprises a flow of whole blood from said source and said flow of anticoagulant, wherein said blood within from said source has a volume, wherein at least part of said flow of anticoagulant is provided to said source, wherein an AC ratio is a ratio of said inlet flow to said flow of anticoagulant, wherein an AC infusion rate is said at least part of said flow of anticoagulant per said volume, and wherein said at least one of said parameters associated with said minimizing step comprises said magnitude of said AC infusion rate and said magnitude of said inlet flow.

20. A method, as claimed in claim 1, wherein:

said associating step comprises optimizing said magnitude of at least one of said parameters.

21. A method, as claimed in claim 1, further comprising the step of:

selecting said predetermined type of blood component based upon at least one of an inventory of said predetermined type of blood component and a demand for said predetermined type of blood component.

22. A method, as claimed in claim 1, further comprising the step of:

maintaining data on said collection procedure for use in subsequent collection procedures performed using said donor.

23. A method, as claimed in claim 1, further comprising the step of:

selecting a type of blood component to be collected from said donor based upon data maintained on said donor for a plurality of collection procedures previously performed on said donor.

24. A method, as claimed in claim 23, wherein:

said data provides an indication that said donor has a propensity to produce a higher yield for a type of blood component from said selecting step versus other types of blood components.

25. A method, as claimed in claim 23, wherein:

said optimizing step is for said first condition, said method further comprising the step of identifying a desired yield of said at least one type of blood component, said associating step comprising performing a first deriving step comprising deriving a magnitude for at least one of said parameters from said providing and identifying steps.

26. A method, as claimed in claim 25, wherein:

one of said parameters is an inlet flow to said blood collection device and another of said parameters is a flow of anticoagulant into said blood component collection system, wherein said inlet flow comprises a flow of whole blood from said source and said flow of anticoagulant, wherein said source of said blood has a volume, wherein an AC ratio is a ratio of said inlet flow to said flow of anticoagulant, and wherein an AC infusion rate is a flow of said anticoagulant provided to said source per said volume of said source.

27. A method, as claimed in claim 26, wherein said performing a first deriving step further comprises:

deriving said magnitude of said inlet flow associated with a predetermined magnitude of said AC infusion rate.

28. A method, as claimed in claim 27, wherein said deriving said magnitude of said inlet flow step comprises:

using said predetermined magnitude of said AC infusion rate and a current magnitude for a total procedure time, said total procedure time being another of said parameters.

29. A method as claimed in claim 28, wherein said deriving said magnitude of said inlet flow step further comprises:

assuming a current magnitude for said inlet flow and performing a first iteration procedure comprising calculating a current magnitude for said AC infusion rate from at least said current magnitude of said inlet flow, evaluating convergence criteria relating to said current magnitude of said inlet flow, and adjusting said current magnitude of said inlet flow and repeating said first iteration procedure step until at least one of third and fourth conditions is satisfied, said third condition being that said convergence criteria is established and said fourth condition being that said first iteration procedure step has been performed a predetermined number of times.

30. A method as claimed in claim 29, wherein:

said deriving said magnitude of said inlet flow step comprises deriving a current magnitude for said AC infusion rate, said performing a first deriving step further comprising performing a second iteration procedure after said deriving said magnitude of said inlet flow step, said second iteration procedure step comprising calculating a current yield from said current magnitude of said inlet flow, said current magnitude of said AC infusion rate, and said current magnitude of said procedure time, comparing said current yield with said desired yield, performing said inputting step after said comparing step when said current yield is within a predetermined amount of said desired yield, adjusting said current magnitude of said total procedure time when said current yield differs from desired yield by more than said predetermined amount, repeating said deriving a magnitude of said inlet flow step after said adjusting said current magnitude of said total procedure time step, and repeating said second iteration procedure step after said repeating said deriving a magnitude of said inlet flow step until at least one of fifth and sixth conditions is satisfied, said fifth condition being that predetermined convergence criteria relating to said current total procedure time is established and said sixth condition being that said second iteration procedure step has been performed a predetermined number of times.

31. A method, as claimed in claim 30, wherein:

said performing a first deriving step further comprises performing a third iteration procedure after said second iteration procedure step and when said at least one of said fifth and sixth conditions is satisfied, said third iteration procedure step comprising adjusting said magnitude of said AC ratio, repeating said first and second iteration procedure steps, and repeating said third iteration procedure step until at least one of seventh and eighth conditions is satisfied, said seventh condition being that predetermined convergence criteria relating to said magnitude of said AC ratio is established and said eighth condition being that said third iteration procedure has been performed a predetermined number of times.

32. A method, as claimed in claim 31, wherein:

said predetermined magnitude of said AC infusion rate is increased by a predetermined amount when at least one of said seventh and eighth conditions is satisfied, wherein said performing a first deriving step further comprises repeating said first, second, and third iteration procedure steps using said increased AC infusion rate.

33. A method, as claimed in claim 28, wherein:

said deriving said magnitude of said inlet flow step comprises deriving a current magnitude for said AC infusion rate, said performing a first deriving step further comprising iteratively calculating a current blood component yield using at least said current magnitude of said inlet flow and said current magnitude of said AC infusion rate and by using said providing step and by iteratively adjusting said magnitude of said current total procedure time until at least one of third and fourth conditions is satisfied, said third condition being achieving said desired yield of blood components and said fourth condition being performing said first iteration procedure step a predetermined number of times.

34. A method, as claimed in claim 28, wherein said performing a first deriving step further comprises deriving a total procedure time, after said deriving said magnitude of said inlet flow step, which provides a current yield.

35. A method, as claimed in claim 26, wherein:

said associating step comprises selecting a maximum magnitude for said AC infusion rate, and wherein said associating step further comprises generating a calculated magnitude of said inlet flow using at least said maximum magnitude of said AC infusion rate.

36. A method, as claimed in claim 35, wherein said performing a first deriving step further comprises:

calculating a theoretical magnitude of said inlet flow which provides a maximum yield of said at least one predetermined blood component and comparing said theoretical and calculated magnitudes of said inlet flow, and wherein said inputting step comprises inputting the lesser of said theoretical magnitude and said calculated magnitude of said inlet flow.

37. A method, as claimed in claim 36, wherein:

another of said parameters is a total procedure time, wherein a current magnitude for said total procedure time is assumed, and wherein said performing a first deriving step further comprises performing a first iteration procedure, said performing a first iteration procedure step comprising calculating a current blood component yield using the lesser of said calculated and theoretical magnitudes of said inlet flow of whole blood, said current magnitude of said total procedure time, and said maximum AC infusion rate, comparing said current blood component yield with said desired blood component yield, and repeating said first iteration procedure using an adjusted current total procedure time until at least one of said third and fourth conditions is satisfied, said third condition being that said current magnitude of said blood component yield is within a predetermined amount of said desired blood component yield and said fourth condition being that said first iteration procedure step has been performed a predetermined number of times.

38. A method as claimed in claim 36, wherein:

another of said parameters is a total procedure time and said performing a first deriving step further comprises assuming a current magnitude for said total procedure time and performing a first iteration procedure, said performing a first iteration procedure step comprising calculating a current yield from the lesser of said actual and theoretical magnitudes of said inlet flows, a maximum magnitude for said AC ratio, and said maximum magnitude of said AC infusion rate, and said current magnitude of said procedure time, comparing said current yield with said desired yield, incrementally adjusting said current magnitude of said total procedure time when said current yield differs from desired yield by more than a predetermined amount, and repeating said first iteration procedure step until at least one of a third and fourth condition is satisfied, said third condition being that said current yield is within said amount of said desired yield and said fourth condition being that said first iteration procedure step has been performed a predetermined number of times.

39. A method, as claimed in claim 26, wherein:

said at least one of said parameters is a total procedure time, said performing a first deriving step comprising maximizing said inlet flow and minimizing said total procedure time.

40. A method, as claimed in claim 25, further comprising the steps of:

providing a magnitude for each of said parameters before said identifying step;

performing said collection procedure on said blood component collection device before said identifying step, using said providing a magnitude step, and for a first time period, wherein said associating step is performed after expiration of said first time period.

41. A method, as claimed in claim 25, wherein:

one of said parameters is a total procedure time, and wherein said performing a first deriving step comprises minimizing said magnitude of said total procedure time based upon said magnitude of at least one of said parameters other than said total procedure time.

42. A method, as claimed in claim 41, wherein:

one of said parameters is an inlet flow to said blood collection device and another of said parameters is a flow of anticoagulant into said blood component collection system, wherein said inlet flow comprises a flow of whole blood from said source and said flow of anticoagulant, wherein said blood within from said source has a volume, wherein at least part of said flow of anticoagulant is provided to said source, wherein an AC ratio is a ratio of said inlet flow to said flow of anticoagulant, wherein an AC infusion rate is said at least part of said flow of anticoagulant per said volume, and wherein said at least one of said parameters associated with said minimizing step comprises said magnitude of said AC infusion rate and said magnitude of said inlet flow.

43. A method, as claimed in claim 23, wherein:

said source is a human donor and said biological data comprises at least one of said donor's hematocrit, height, weight, and sex.

44. A method for collecting a blood component from a source of whole blood using a blood component collection system comprising a blood component collection device and collection procedure, wherein an inlet flow to said blood component collection system comprises a flow of whole blood from said source and a flow of anticoagulant, said method comprising the steps of:

identifying a total procedure time for a collection procedure to be performed on a source of whole blood to obtain a plurality of at least one type of blood component therefrom using a blood component collection system comprising a blood component collection device and said collection procedure;

deriving a first inlet flow to said collection system which provides a maximum yield of said blood components;

deriving a second inlet flow to said collection system using at least said identifying a total procedure time step;

identifying a smallest magnitude of said first and second inlet flows as an actual inlet flow to said blood component collection system; and performing said collection procedure with said blood component collection device, using said actual inlet flow, and for said total procedure time to collect said blood components from said source of whole blood.

45. A method, as claimed in claim 44, wherein:

wherein said blood within said source has a volume, wherein at least part of said flow of anticoagulant is provided to said volume, wherein an AC ratio is a ratio of said inlet flow to said flow of anticoagulant, wherein an AC infusion rate is said at least part of said flow of anticoagulant per said volume, and wherein said deriving a second inlet flow step further uses a maximum AC ratio and a maximum AC infusion rate.

46. A method, as claimed in claim 44, wherein:

said source is a human donor, wherein said method further comprises the step of providing biological data relating to said donor comprising at least one of said donor's hematocrit, height, weight, and sex, and wherein at least one of said deriving steps further comprises using said providing biological data step.

47. A method, as claimed in claim 44, wherein:

said source of said blood has a volume, wherein an AC ratio is a ratio of said inlet flow to said flow of anticoagulant, and wherein an AC infusion rate is a flow of said anticoagulant provided to said source per said volume of said source.

48. A method, as claimed in claim 47, wherein said deriving a second inlet flow step comprises:

deriving a magnitude of said second inlet flow associated with a predetermined magnitude of said AC infusion rate.

49. A method, as claimed in claim 48, wherein said deriving a second inlet flow step further comprises:

using said predetermined magnitude of said AC infusion rate.

50. A method as claimed in claim 49, wherein said deriving a second inlet flow step further comprises:

assuming a current magnitude for said second inlet flow and performing a first iteration procedure comprising calculating a current magnitude for said AC infusion rate from at least said current magnitude of said second inlet flow, evaluating convergence criteria relating to said current magnitude of said inlet flow, and adjusting said current magnitude of said inlet flow and repeating said first iteration procedure until at least one of first and second conditions is established, said first condition being that said convergence criteria is established and said second condition being that said first iteration procedure step has been performed a predetermined number of times.

51. A method, as claimed in claim 47, further comprising the step of:

selecting a maximum magnitude for said AC infusion rate, wherein said deriving a second inlet flow step further comprises using at least said maximum magnitude of said AC infusion rate.

52. A method, as claimed in claim 44, further comprising the step of:

selecting said predetermined type of blood component based upon at least one of an inventory of said predetermined type of blood component and a demand for said predetermined type of blood component.

53. A method, as claimed in claim 44, further comprising the step of:

selecting a type of blood component to be collected from said donor based upon data maintained on said donor for a plurality of collection procedures previously performed on said donor.

54. A method, as claimed in claim 53, wherein:

said data provides an indication that said donor has a propensity to produce higher yield for a type of blood component from said selecting step versus other types of blood components.

55. A method, as claimed in claim 44, further comprising the step of:

maintaining data on said collection procedure for use in subsequent collection procedures performed using said donor.

56. A method for collecting a blood component from a donor using a blood component collection system comprising a blood component collection device and a collection procedure, said collection procedure comprising a plurality of parameters, said method comprising the steps of:

providing biological data relating to a donor;

associating a magnitude with a plurality of control parameters associated with a collection procedure to be performed on blood from said donor to obtain a plurality of at least one type of blood component therefrom using a blood component collection system, said blood component collection system comprising a blood component collection device and said collection procedure, said associating step being based upon at least said providing step;

optimizing said magnitude of at least one of said control parameters in relation to both donor constraints and system constraints, said optimizing step allowing for achieving at least one of first and second conditions, said first condition being collecting a predetermined quantity of said blood components in a minimum amount of time and said second condition being collecting a maximum quantity of said blood components in a predetermined amount of time;

inputting said magnitudes of said parameters into said blood component collection device after said optimizing step; and performing said collection procedure on said blood component collection device using said parameters to collect said blood components from said donor to achieve at least one of said first and second conditions.

57. A method, as claimed in claim 56, further comprising the step of:

selecting said predetermined type of blood component based upon at least one of an inventory of said predetermined type of blood component and a demand for said predetermined type of blood component.

58. A method, as claimed in claim 56, further comprising the step of:

selecting a type of blood component to be collected from said donor based upon data maintained on said donor for a plurality of collection procedures previously performed on said donor.

59. A method, as claimed in claim 58, wherein:

said data provides an indication that said donor has a propensity to produce higher yield for said selected type of blood component versus other types of blood components.

60. A method, as claimed in claim 56, further comprising the step of:

maintaining data on said collection procedure for use in subsequent collection procedures performed using said donor.

61. A blood component collection system, comprising:

means for providing biological data relating to a source of whole blood comprising a plurality of blood component types, said source comprising a human donor and said data comprising at least one of said donor's hematocrit, height, weight and sex;

a blood component collection device;

means for identifying a desired yield for at least one predetermined blood component type;

a collection procedure having a plurality of parameters associated therewith;

means for associating a magnitude with each of said parameters, said means for associating comprising first means for deriving a magnitude for at least one of said parameters from said means for providing and said means for identifying; and means for inputting said magnitude of each said parameter.

62. A system, as claimed in claim 61, wherein:

said biological data comprises said donor's hematocrit, height, weight, and sex.

63. A system, as claimed in claim 61, wherein:

one of said parameters is an inlet flow to said blood collection device and another of said parameters is a flow of anticoagulant into said blood component collection system, wherein said inlet flow comprises a flow of whole blood from said source and said flow of anticoagulant, wherein said source of said blood has a volume, wherein at least part of said flow of anticoagulant is provided to said source, wherein an AC ratio is a ratio of said inlet flow to said flow of anticoagulant, and wherein an AC infusion rate is a flow of said anticoagulant provided to said source per said volume of said source.

64. A system, as claimed in claim 63, wherein:

said means for associating comprises means for selecting a maximum magnitude for said AC infusion rate, and wherein said means for associating further comprises means for generating a calculated magnitude of said inlet flow using at least said maximum magnitude of said AC infusion rate.

65. A system, as claimed in claim 64, wherein said first means for deriving further comprises:

means for calculating a theoretical magnitude of said inlet flow which provides a maximum yield of said at least one predetermined blood component and means for comparing said theoretical and calculated magnitudes of said inlet flow, wherein said means for inputting comprises means for inputting the lesser of said theoretical magnitude and said calculated magnitude of said inlet flow.

66. A system, as claimed in claim 65, wherein:

another of said parameters is a total procedure time, wherein a current magnitude for said total procedure time is assumed, and wherein said first means for deriving further comprises means for performing a first iteration procedure, said means for performing a first iteration procedure comprising means for calculating a current blood component yield using the lesser of said calculated and theoretical magnitudes of said inlet flow of whole blood, said current magnitude of said total procedure time, and said maximum AC infusion rate, means for comparing said current blood component yield with said desired blood component yield, and means for repeating said means for performing a first iteration procedure using an adjusted current total procedure time until at least one of first and second conditions is satisfied, said first condition being that until said current magnitude of said blood component yield is within a predetermined amount of said desired blood component yield, said second condition being that said means for performing a first iteration procedure has been performed a predetermined number of times.

67. A system, as claimed in claim 65, wherein:

another of said parameters is a total procedure time and said first means for deriving further comprises means for assuming a current magnitude for said total procedure time and means for performing a first iteration procedure, said means for performing a first iteration procedure comprising means for calculating a current yield from the lesser of said actual and theoretical magnitudes of said inlet flows, a maximum magnitude for said AC ratio, and said maximum magnitude of said AC infusion rate, and said current magnitude of said procedure time, means for comparing said current yield with said desired yield, means for incrementally adjusting said current magnitude of said total procedure time when said current yield differs from desired yield by more than a predetermined amount, and means for repeating said means for performing a first iteration procedure until at least one of a first and second condition is satisfied, said first condition being that said current yield is within said first predetermined amount of said desired yield and said second condition being that said first iteration procedure has been performed a predetermined number of times.

68. A system, as claimed in claim 63, wherein said first means for deriving comprises:

means deriving said magnitude of said inlet flow associated with a predetermined magnitude of said AC infusion rate.

69. A system, as claimed in claim 68, wherein said means for deriving said magnitude of said inlet flow uses said predetermined magnitude of said AC infusion rate and a current magnitude for a total procedure time, said total procedure time being another of said parameters.

70. A system, as claimed in claim 69, wherein said means for deriving said magnitude of said inlet flow further comprises:

means for performing a first iteration procedure comprising means for calculating a current magnitude for said AC infusion rate from at least said current magnitude of said inlet flow, wherein a first said current magnitude of said inlet flow is initially assumed, said means for performing a first iteration procedure further comprising means for evaluating convergence criteria relating to said current magnitude of said inlet flow, and means for adjusting said current magnitude of said inlet flow, and means for repeating said means for performing a first iteration procedure until at least one of first and second conditions is established, said first condition being that said convergence criteria is established and said second condition being that said means for performing a first iteration procedure has been performed a predetermined number of times.

71. A system, as claimed in claim 70, wherein:

said means for deriving said magnitude of said inlet flow comprises means for deriving a current magnitude for said AC infusion rate, said first means for deriving further comprising means for performing a second iteration procedure after said means for deriving said magnitude of said inlet flow, said means for performing a second iteration procedure comprising means for calculating a current yield from said current magnitude of said inlet flow, said current magnitude of said AC infusion rate, and said current magnitude of said procedure time, means for comparing said current yield with said desired yield, means for performing said means for inputting after said means for comparing when said current yield is within a predetermined amount of said desired yield, means for adjusting said current magnitude of said total procedure time when said current yield differs from desired yield by more than said predetermined amount, means for repeating said means for deriving a magnitude of said inlet flow after said means for adjusting said current magnitude of said total procedure time, and means for repeating said means for performing a second iteration procedure until at least one of third and fourth conditions is satisfied, said third condition being that predetermined convergence criteria relating to said current total procedure time is established, said fourth condition being that said means for performing a second iteration procedure has been performed a predetermined number of times.

72. A system, as claimed in claim 71, wherein:

said first means for deriving further comprises means for performing a third iteration procedure after said means for performing a second iteration procedure and when at least one of said third and fourth conditions associated with said means for performing a second iteration procedure is satisfied, said means for performing a third iteration procedure comprising means for adjusting said magnitude of said AC ratio, means for repeating said means for performing said first and second iteration procedures, and means for repeating said means for performing a third iteration procedure until at least one of fifth and sixth conditions is satisfied, said fifth condition being that predetermined convergence criteria relating to said magnitude of said AC ratio is established and said sixth condition being that said means for performing a third iteration procedure has been performed a predetermined number of times.

73. A system, as claimed in claim 72, wherein:

said predetermined magnitude of said AC infusion rate is increased by a predetermined amount when at least one of said fifth and sixth conditions associated with said means for performing a third iteration procedure is satisfied, wherein said first means for deriving further comprises means for repeating said means for performing first, second, and third iteration procedures using said increased AC infusion rate.

74. A system, as claimed in claim 69, wherein:

said means for deriving said magnitude of said inlet flow comprises means for deriving a current magnitude for said AC infusion rate, said first means for deriving further comprising means for iteratively calculating a current blood component yield using at least said current magnitude of said inlet flow and said current magnitude of said AC infusion rate and by using said means for providing and by iteratively adjusting said magnitude of said current total procedure time until at least one of first and second conditions is established, said first condition being within a predetermined variance of said desired yield of blood components and said second condition being when said magnitude of said current total procedure time has been adjusted a predetermined number of times.

75. A system, as claimed in claim 69, wherein said first means for deriving further comprises means for deriving said total procedure time, after said means deriving said magnitude of said inlet flow, which provides a current yield within a predetermined amount of said desired yield.

76. A system, as claimed in claim 63, wherein:

said at least one of said parameters is a total procedure time, said first means for deriving comprising means for maximizing said inlet flow and means for minimizing said total procedure time.

77. A system, as claimed in claim 61, wherein:

one of said parameters is a total procedure time, and wherein said first means for deriving comprises means for minimizing said magnitude of said total procedure time based upon said magnitude of at least one of said parameters other than said total procedure time.

78. A system, as claimed in claim 77, wherein:

one of said parameters is an inlet flow to said blood collection device and another of said parameters is a flow of anticoagulant into said blood component collection system, wherein said inlet flow comprises a flow of whole blood from said source and said flow of anticoagulant, wherein said blood within from said source has a volume, wherein at least part of said flow of anticoagulant is provided to said source, wherein an AC ratio is a ratio of said inlet flow to said flow of anticoagulant, wherein an AC infusion rate is said at least part of said flow of anticoagulant per said volume, and wherein said at least one of said parameters associated with said means for minimizing comprises said magnitude of said AC infusion rate and said magnitude of said inlet flow.

79. A method, as claimed in claim 61, wherein:

said means for associating comprises means for optimizing said magnitude of at least one of said parameters.

80. A blood component collection system, comprising:

a blood component collection system comprising a blood component collection device;

a collection procedure, wherein an inlet flow to said blood component collection system comprises a flow of whole blood from a source and a flow of anticoagulant;

means for identifying a total procedure time for said collection procedure;

means for deriving a first inlet flow to said collection system which provides a maximum yield of said blood components;

means for deriving a second inlet flow to said collection system using at least said means for identifying a total procedure time;

means for identifying a smallest magnitude of said first and second inlet flows as an actual inlet flow to said blood component collection system; and means for performing said collection procedure with said blood component collection device, using said actual inlet flow, and for said total procedure time to collect said blood components from said source of whole blood.

81. A blood component collection system, comprising:

a blood component collection device;

a collection procedure comprising a plurality of parameters;

means for providing biological data relating to a donor;

means for associating a magnitude with each said control parameter based upon at least said means for providing;

means optimizing said magnitude of at least one of said control parameters in relation to both donor constraints and system constraints, said means for optimizing allowing for achieving at least one of first and second conditions, said first condition being collecting a predetermined quantity of said blood components in a minimum amount of time and said second condition being collecting a maximum quantity of said blood components in a predetermined amount of time;

means for inputting said magnitudes of said parameters into said blood component collection device after said means for optimizing; and means for performing said collection procedure on said blood component collection device using said parameters to collect said blood components from said donor to achieve at least one of said first and second conditions.

\* \* \* \* \*

UNITED STATES PATENT AND TRADEMARK OFFICE
CERTIFICATE OF CORRECTION

PATENT NO. : 5,496,265                               Page 1 of 2
DATED      : March 5, 1996
INVENTOR(S): Langley et al.

It is certified that error appears in the above-identified patent and that said Letters Patent is hereby corrected as shown below:

On page 1, under the section "Related U.S. Application Data", please delete the word "abandoned" on line 2 and insert therefor -- pending --. On line 3, please delete the word "abandoned" and insert therefor -- Patent No. 5,421,812 --.

In column 1, line 9, please delete "now abandoned" and insert therefor -- pending --. On line 11, please delete "now abandoned" and insert therefor -- U.S. Patent No. 5,421,812 --.

In column 3, lines 66 and 67, please delete "in place thereof."

In column 10, equation 5, line 21, please delete "$\leq$" and insert therefor -- $\geq$ --.

In column 12, line 7, please delete "7"" and insert therefor -- 7' --.

In column 16, line 25, please delete "and".

UNITED STATES PATENT AND TRADEMARK OFFICE
CERTIFICATE OF CORRECTION

PATENT NO. : 5,496,265
DATED : March 5, 1996
INVENTOR(S) : Langley et al.

It is certified that error appears in the above-indentified patent and that said Letters Patent is hereby corrected as shown below:

In column 26, Claim 25, line 31, please delete "23" and insert therefor -- 56 --.

In column 29, Claim 43, line 40, please delete "23" and insert therefor -- 56 --.

Signed and Sealed this

Eleventh Day of February, 1997

Attest:

BRUCE LEHMAN

Attesting Officer

Commissioner of Patents and Trademarks